(12) United States Patent
Euteneuer et al.

(10) Patent No.: US 10,039,544 B2
(45) Date of Patent: Aug. 7, 2018

(54) FASTENERS AND FASTENER DELIVERY DEVICES FOR AFFIXING SHEET-LIKE MATERIALS TO BONE OR TISSUE

(71) Applicant: Rotation Medical, Inc., Plymouth, MN (US)

(72) Inventors: Charles L. Euteneuer, St. Michael, MN (US); Rebecca McCarville, Spring Park, MN (US)

(73) Assignee: Rotation Medical, Inc., Plymouth, MN (US)

( * ) Notice: Subject to any disclaimer, the term of this patent is extended or adjusted under 35 U.S.C. 154(b) by 0 days.

(21) Appl. No.: 15/824,497

(22) Filed: Nov. 28, 2017

(65) Prior Publication Data

US 2018/0078254 A1 Mar. 22, 2018

Related U.S. Application Data

(63) Continuation of application No. 15/207,075, filed on Jul. 11, 2016, now Pat. No. 9,855,037, which is a
(Continued)

(51) Int. Cl.

| *A61B 17/064* | (2006.01) |
|---|---|
| *A61B 17/56* | (2006.01) |
| *A61B 17/88* | (2006.01) |
| *A61B 17/84* | (2006.01) |
| A61B 17/04 | (2006.01) |
| A61B 17/068 | (2006.01) |
| A61B 17/08 | (2006.01) |

(52) U.S. Cl.
CPC ........ *A61B 17/0642* (2013.01); *A61B 17/064* (2013.01); *A61B 17/0644* (2013.01); *A61B 17/08* (2013.01); *A61B 17/56* (2013.01); *A61B 17/84* (2013.01); *A61B 17/844* (2013.01); *A61B 17/88* (2013.01); *A61B 17/0643* (2013.01); *A61B 17/0682* (2013.01); *A61B 2017/0403* (2013.01); *A61B 2017/0432* (2013.01); *A61B 2017/081* (2013.01); *A61B 2017/564* (2013.01); *A61B 2218/00* (2013.01)

(58) Field of Classification Search
CPC .............. A61B 17/064; A61B 17/0642; A61B 17/0643; A61B 17/0644; A61B 17/0682; A61B 2017/564; A61B 17/58; A61B 17/68; A61B 17/84; A61B 17/844; A61B 17/88; B60D 1/02; E01B 9/12; F16B 13/04; F16B 15/06
See application file for complete search history.

(56) References Cited

U.S. PATENT DOCUMENTS 4,434,796 A * 3/1984 Karapetian ........ A61B 17/0642
606/138

* cited by examiner

*Primary Examiner* — Larry E Waggle, Jr.
(74) *Attorney, Agent, or Firm* — Seager, Tufte & Wickhem LLP

(57) ABSTRACT

A fastener for attaching a sheet-like implant to tissue or bone. The fastener includes a first arm having a proximal end and a distal end, a second arm having a proximal end and a distal end, and a bridge extending therebetween. Each of the first and second arms include a trunk portion defining at least a portion thereof, the trunk portion having a cavity therein and an aperture through a wall thereof. A claw is disposed in the cavity which is moveable from a first delivery position to a second deployed position. A pull member engages each claw to move the claw from the delivery position to the deployed position.

20 Claims, 20 Drawing Sheets

Related U.S. Application Data continuation of application No. 14/721,617, filed on May 26, 2015, now Pat. No. 9,414,841, which is a continuation of application No. 13/717,515, filed on Dec. 17, 2012, now Pat. No. 9,107,661.

(60) Provisional application No. 61/577,632, filed on Dec. 19, 2011.

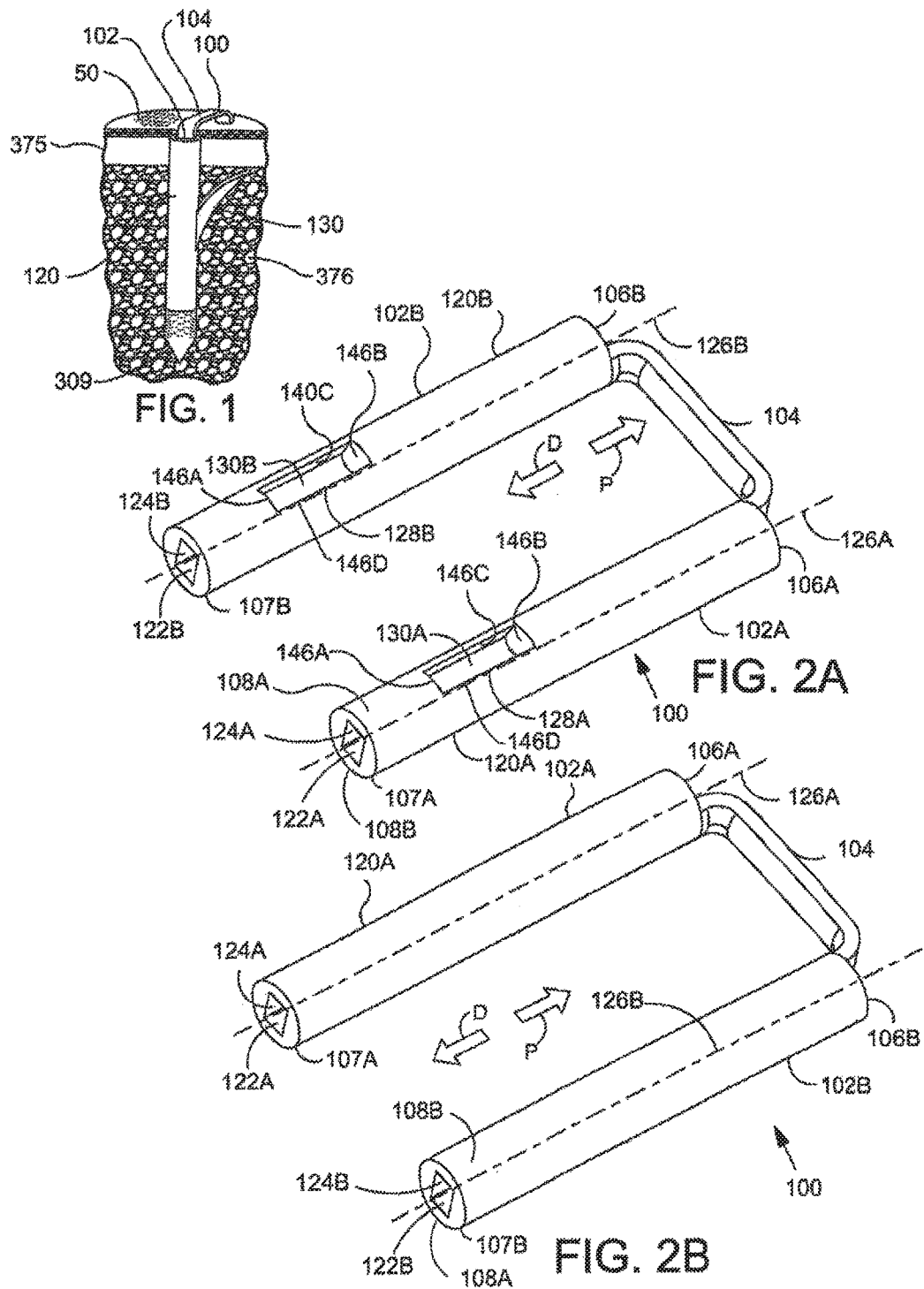

FASTENERS AND FASTENER DELIVERY DEVICES FOR AFFIXING SHEET-LIKE MATERIALS TO BONE OR TISSUE

CROSS REFERENCE TO RELATED APPLICATIONS

This application is a continuation of U.S. application Ser. No. 15/207,075 filed on Jul. 11, 2016, which is a continuation of U.S. application Ser. No. 14/721,617 filed on May 26, 2015, which is a continuation of U.S. application Ser. No. 13/717,515, filed on Dec. 17, 2012, which claims the benefit of U.S. Provisional Patent Application Ser. No. 61/577,632 filed on Dec. 19, 2011, the disclosures of each incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for delivery and fixation of sheet-like materials, such as for treating tendons or like tissue of articulating joints, such as tendons in the rotator cuff of the shoulder.

BACKGROUND OF THE INVENTION

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. The rotator cuff muscles are a complex of muscles. The muscles of the rotator cuff include the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoral muscle forces.

The muscles of the rotator cuff arise from the scapula. The distal tendons of the rotator cuff muscles splay out and interdigitate to form a common continuous insertion on the humerus. The supraspinatus muscle arises from the supraspinatus fossa of the posterior scapula, passes beneath the acromion and the acromioclavicular joint, and attaches to the superior aspect of the greater tuberosity. The mechanics of the rotator cuff muscles are complex. The rotator cuff muscles rotate the humerus with respect to the scapula, compress the humeral head into the glenoid fossa providing a critical stabilizing mechanism to the shoulder (known as concavity compression), and provide muscular balance. The supraspinatus and deltoid muscles are equally responsible for producing torque about the shoulder joint in the functional planes of motion.

The rotator cuff muscles are critical elements of this shoulder muscle balance equation. The human shoulder has no affixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury or damage. Additionally, the strain or tear can occur within the tendon itself. Injuries to the supraspinatus tendon and current modalities for treatment are defined by the type and degree of tear. The first type of tear is a full thickness tear, which as the term indicates is a tear that extends through the thickness of the supraspinatus tendon regardless of whether it is completely torn laterally. The second type of tear is a partial thickness tear which is further classified based on how much of the thickness is torn, whether it is greater or less than about 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the current standard treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, and rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial thickness tear is not repaired. Several authors have reported satisfactory early post operative results from these procedures, but over time recurrent symptoms have been noted. In the event of recurrent symptoms, many times a patient will "live with the pain". This may result in less use of the arm and shoulder which causes further degeneration of the tendon and may lead to more extensive damage. A tendon repair would then need to be done in a later procedure if the prescribed treatment for the partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. Further, it would be beneficial to be able to treat partial thickness tears greater than 50% without cutting the untorn portion of the tendon to complete the tear before suturing back together. There is a large need for surgical techniques and systems to treat partial thickness tears and prevent future tendon damage by strengthening or repairing the native tendon having the partial thickness tear.

SUMMARY OF THE INVENTION

Some aspects of the present disclosure are directed to a fastener or staple that can be used to attach an implant to bone. According to other aspects, the staple or fastener can be included in a kit or system that also can include a staple delivery device and a pilot hole forming trocar assembly. The trocar assembly is used to create pilot holes and retain instrument position with respect to those pilot holes for staple insertion. The staple delivery device can carry the staple into the pilot holes and release the staple in engagement with bone to retain the implant in position.

The fastener or staple can also include, in some embodiments, a first arm having a proximal end and a distal end, a second arm having a proximal end and a distal end, and a bridge connecting the first arm and second arm, wherein each of the first and second arms include a trunk portion extending over at least a portion of the length thereof. Each trunk can have a cavity therein and an aperture through a wall of each trunk to the cavity. In some embodiments, each of the cavities is a lumen defined by a wall of each trunk having an inner surface defining the lumen extending along a longitudinal axis with the aperture extending through this wall.

Each trunk can also include a claw disposed in each cavity of each trunk wherein each of the claws is moveable from a first retracted position for delivery of the staple to a second deployed position having a portion of the claw extending through the aperture in active engagement with bone when implanted therein. Further each of the claws can include a head, the head including an anterior edge opposite a posterior edge, a tail of the first claw abutting the posterior edge of the head, wherein the head of each claw is disposed completely within the cavity of the trunk in the delivery position.

Each claw can extend across the lumen of its respective trunk with the anterior edge of the head extending into the aperture and the tail extending through the aperture when the staple is in the deployed configuration. The head can be shaped and dimensioned such that camming forces applied to the wall by the anterior edge of the head as the claw moves between the delivery position and the deployed position urge a portion of the wall toward an elastically deflected shape.

Each head of each claw can have a major axis and a minor axis that is perpendicular to the major axis, the head having a length measured along the major axis and a width measured along the minor axis, the length being greater than the width. Further, the length of the head can be greater than a diameter of the lumen and the width of the head can be less than the diameter of the lumen. The major axis of the head can be generally parallel to the longitudinal axis of the lumen when each claw is in the delivery position and the major axis of the head can extend in a direction transverse to the longitudinal axis of the lumen when each claw is in the deployed position. The minor axis of the head can extend in a direction transverse to the longitudinal axis of the lumen when each claw is in the delivery position and the minor axis of the head can be generally parallel to the longitudinal axis of the lumen when each claw is in the deployed position.

In some embodiments, the fastener includes a pull member releasably engaging each of the claws to move the claw from the first to the second position. The pull member can be a rod releasably connected to a slot or notch in each claw. Alternatively, the pull member can be a suture extending through a hole defined by each claw such that the suture can be disconnected from the first claw by pulling one end of the suture through the hole.

BRIEF DESCRIPTION OF THE DRAWINGS

FIG. 1 is a perspective view in partial cross section illustrating an exemplary tissue fastener or staple in accordance with the present disclosure as deployed in bone;

FIGS. 2A and 2B are alternative perspective views of the tissue fastener or staple of FIG. 1 illustrating other features in accordance with the present disclosure;

DETAILED DESCRIPTION OF THE INVENTION

Figure 3A:
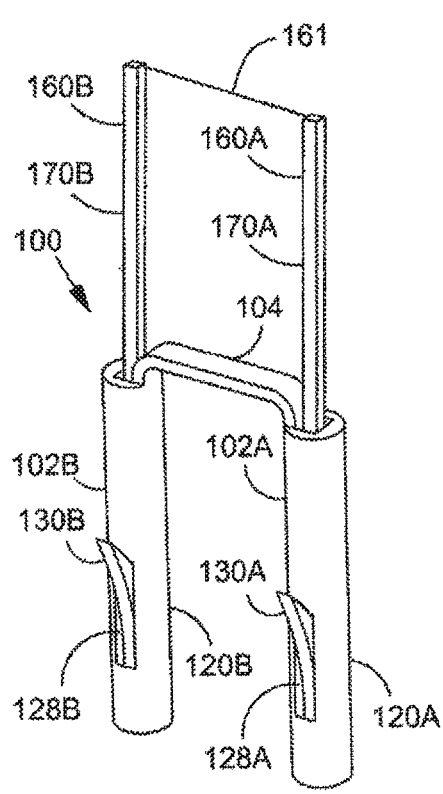
FIGS. 3A-3E are schematic perspective views of the operable components of the exemplary tissue fastener prior to deployment in bone illustrating a projection deployment member.

The following detailed description should be read with reference to the drawings in which similar elements in different drawings are numbered the same. The drawings, which are not necessarily to scale, depict illustrative embodiments and are not intended to limit the scope of the invention.

FIG. 1 is a perspective view illustrating an exemplary staple 100 in accordance with the present detailed description. The staple is depicted deployed in bone with the bone shown in partial cross section so that features of the staple can be viewed. In particular, the staple 100 includes a bridge 104 that connects two longitudinally extending arms 102 (only one arm 102A is visible in FIG. 1). At least a portion of each arm includes a trunk 120 which may extend for the full length of the arm or only a portion of the length. If the trunk 120 extends for only a portion of the arm, then a non-trunk portion of the arm will connect the trunk to the bridge.

The staple is illustrated deployed in bone having a cortical layer 375 and a cancellous portion 376. The staple is deployed in pilot holes 309, as later described herein. Further, each trunk includes a claw portion 130 that is moveable from a retracted or stowed position within the trunk 120 to a deployed or extended position as shown in FIG. 1. In the extended position, the claw 130 interacts with the bone providing pullout strength when force is applied to the bridge, such as force applied to an implant 50 as illustrated.

FIG. 2A and FIG. 2B are perspective views illustrating the staple 100 of FIG. 1 in alternative views, with the staple rotated 180 degrees in FIG. 2B from FIG. 2A so that in combination both sides of the staple are viewed. FIG. 2A and FIG. 2B may be collectively referred to as FIG. 2. Staple 100 comprises a first arm 102A and a second arm 102B. A bridge 104 of staple 100 can be seen extending between the proximal end of first arm 102A and the proximal end of second arm 102B. A proximal direction P and a distal direction D are illustrated with arrows in FIG. 2.

In the embodiment of FIG. 2, each arm 102A, 102B include a first trunk 120A and a second trunk 120B, respectively. As illustrated the trunks extend for substantially the entire length of the arms 102A, 102B. However, this length may be varied in alternative embodiments. First trunk 120A of staple 100 comprises a first wall defining a first lumen 124A. A first claw 130A is at least partially disposed in first lumen 124A. The first trunk 120A also defines a first aperture 128A that fluidly communicates with first lumen 124A. In the embodiment of FIG. 2, first aperture 128A is disposed on a first side 108A of staple 100 shown as the top in FIG. 2A. First side 108A is generally opposite a second side 108B of staple 100 which is shown as the top in FIG. 2B. First claw 130A can be seen fully retracted or stowed within first aperture 128A.

Second trunk 120B of staple 100 comprises a second wall that defines a second lumen 124B. Second claw 130B is disposed in second lumen 124B in the embodiment of FIG. 2. The second trunk 120B also defines a second aperture 128B that fluidly communicates with second lumen 124B. The second aperture 128B is disposed on the first side 108A of staple 100. Second claw 130B can be seen fully retracted or stowed in second aperture 128B.

In the embodiment of FIG. 2, first lumen 124A extends along a first longitudinal axis 126A and second lumen 124B extends along a second longitudinal axis 126B. When first claw 130A is in the deployed position, a distal portion of first claw 130A extends in a direction transverse to first longitudinal axis 126A. Similarly, second claw 130B extends in a direction transverse to second longitudinal axis 126B when second claw 130B is in the deployed position. When first claw 130A extends in a direction transverse to first longitudinal axis 126A and second claw 130B extends in a direction transverse to second longitudinal axis 126B, the claws may act to retain staple 100 in a tissue.

As illustrated in FIG. 2A, each aperture 128 is defined by a plurality of edge surfaces of the wall defining that aperture. More particularly, in the exemplary embodiment of FIG. 2A, each aperture 128 is defined by a proximal edge surface 146B, a distal edge surface 146A, and two side edge surfaces 146C and 146D.

Figure 3B:
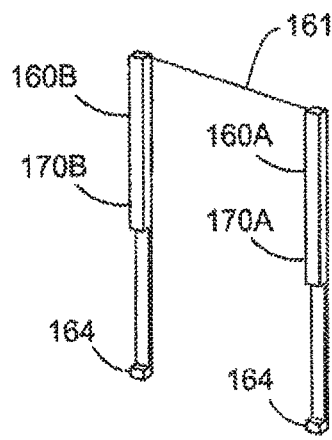
Figure 3C:
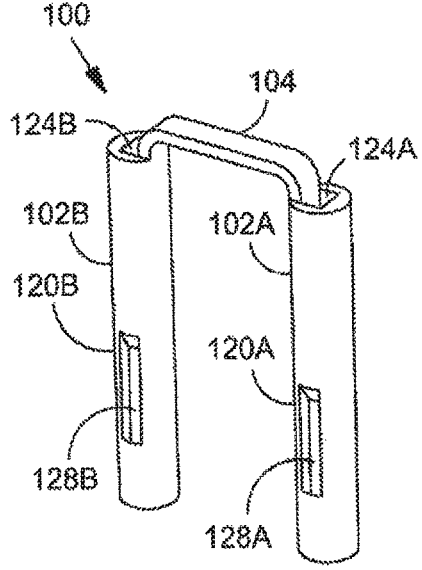
Figure 3D:
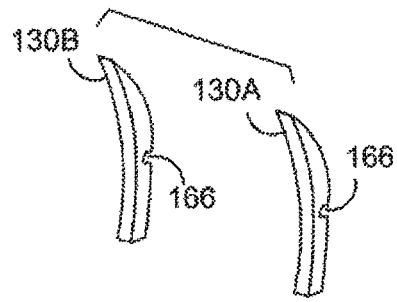

FIG. 3A is a perspective view illustrating an exemplary assembly in accordance with this detailed description. FIGS. 3B-3D are additional perspective views showing the individual components of the assembly of FIG. 3A in an exploded state. FIG. 3A-3D may be collectively referred to as FIG. 3. Staple 100 of FIG. 3 comprises a first arm 102A and a second arm 102B. A bridge 104 of staple 100 can be seen extending between the proximal end of first arm 102A and the proximal end of second arm 102B.

First trunk 120A of staple 100 comprises a first wall defining a first lumen 124A. A first claw 130A is partially disposed in first lumen 124A in the embodiment of FIG. 3A. First trunk 120A also defines a first aperture 128A that fluidly communicates with first lumen 124A. A portion of first claw 130A be seen extending beyond first aperture 128A in FIG. 3A. Second trunk 120B also defines a second aperture 128B that fluidly communicates with second lumen 124B. A portion of second claw 130B can be seen extending beyond second aperture 128B in FIG. 3A.

In FIG. 3A, a first pull member 160A can be seen extending into first lumen 124A of first trunk 120A. In the embodiment of FIG. 3, first pull member 160A comprises a first control rod 170A that is slidably disposed in first lumen 124A of first trunk 120A. First control rod 170A and first claw 130A engage each other to form a mechanically interlocking, but releasable connection. The connection between first control rod 170A and first claw 130A is configured such that a proximally directed force applied to first control rod 170A is transferred to first claw 130A to urge movement of first claw 130A between a delivery or retracted position and a deployed position. In the exemplary embodiment of FIG. 3, first control rod 170 includes a tab 164 that is received in a slot or notch 166 defined by first claw 130A.

In FIG. 3A, a second pull 160B can be seen extending into second lumen 124B of second trunk 120B. In the embodiment of FIG. 3, second pull 160B comprises a second control rod 170B that is slidably disposed in second lumen 124B of second trunk 120B. Second control rod 170B and second claw 130B engage each other to form a mechanically interlocking, but releasable connection. The connection between second control rod 170B and second claw 130B is configured such that a proximally directed force applied to second control rod 170B is transferred to second claw 130B to urge movement of second claw 130B between a delivery or retracted position and a deployed position. In the exemplary embodiment of FIG. 3, second control rod 170 includes a tab 164 that is received in a notch 166 defined by second claw 130B. The proximal end of second pull 160B is depicted as coupled to the proximal end of first pull 160A so that proximally directed forces may be simultaneously applied to first claw 130A and second claw 130B.

Figure 3E:
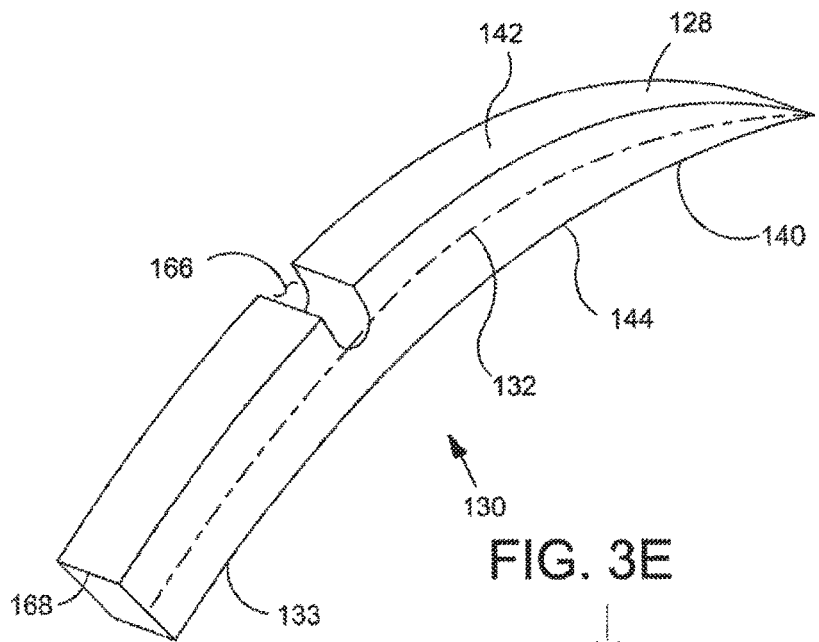

FIG. 3E is a perspective view of an exemplary claw 130 in accordance with this detailed description. In the embodiment of FIG. 3E, claw 130 comprises a body 133 including an upper surface 138 and a lower surface 140. Upper surface 138 and lower surface 140 are on opposite sides of claw 130. In the embodiment of FIG. 3E, body 133 extends along a curvilinear axis 132. Upper surface 138 and lower surface 140 are separated by the height of body 133. Body 133 has a tapering shape such that the height of body 133 changes along curvilinear axis 132. In some useful embodiments, the height of body 133 is selected so that an interference fit is formed between claw 130 and an aperture defined by a trunk when claw 130 is disposed in a deployed position (as illustrated in the previous Figure).

The proximal end of first claw 130A comprises a knife edge 168. In some useful embodiments, the shape of knife edge 168 is sufficiently sharp so that knife edge 168 cuts into at least a portion of the thickness or through the inner surface of a wall of trunk 120 when claw 130 is assuming a deployed position relative to a trunk to retain the deployed position. In the embodiment of FIG. 3E, upper surface 138 of first claw 130A includes a convex surface 142. Also in the embodiment of FIG. 3E, lower surface 140 of first claw 130A comprises a concave surface 144. Body 133 of claw 130 defines a notch 166. In some useful embodiments, notch 166 is dimensioned to receive a tab, for example, the tab illustrated in the previous Figure.

Figure 4A:
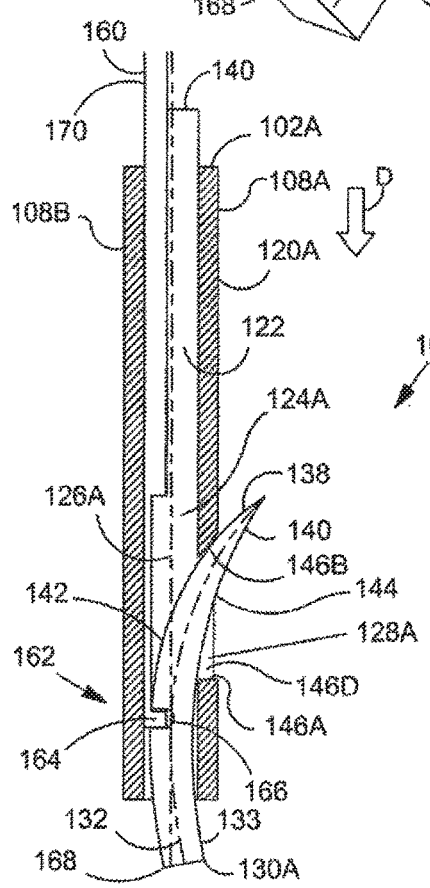
FIGS. 4A-4B are partial cross sectional views of the fastener of FIG. 1 depicting a projection in a first retracted state and a second deployed or extended state, respectively.
Figure 4B:
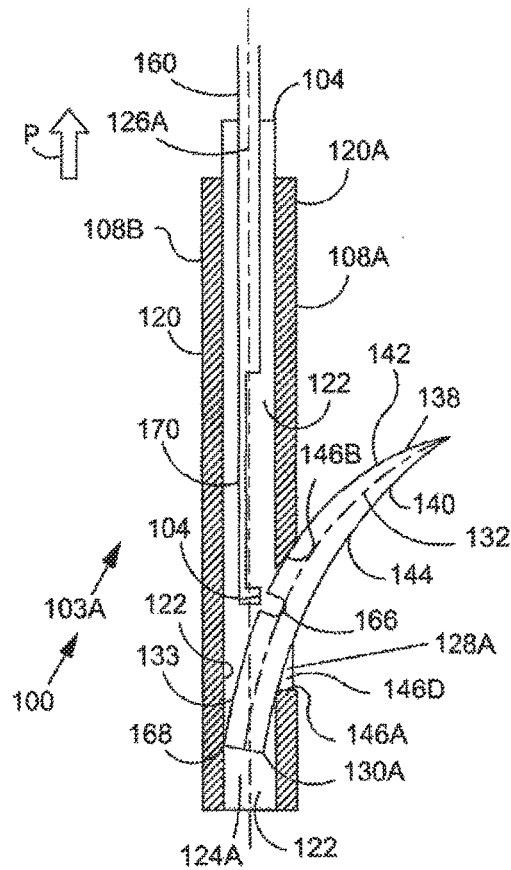

FIG. 4A and FIG. 4B are cross-sectional views illustrating an exemplary staple 100 in accordance with this detailed description. Staple 100 of FIG. 4 includes first trunk assembly 103A. First trunk assembly 103A includes a first claw 130A that is partially disposed in a first lumen 124A defined by a first trunk 120A. First claw 130A is disposed in a delivery or retracted position in the embodiment of FIG. 4A. In the embodiment of FIG. 4B, however, first claw 130A is disposed in a deployed position. Methods in accordance with this detailed description may include the step of moving a claw from a delivery or retracted position (e.g., the delivery position of FIG. 4A) to a deployed position (e.g., the deployed position of FIG. 4B).

Staple 100 includes first trunk 120A and a second trunk (not visible in FIG. 4). A bridge 104 of staple 100 extends from the proximal end of first arm 102A to the proximal end of the second arm. First trunk 120A of staple 100 includes a wall 120 having an inner surface 122 defining first lumen 124A. In the embodiment of FIG. 4, first lumen 124A extends along a first longitudinal axis 126A. Wall 120 of first trunk 120A also defines a first aperture 128A that fluidly communicates with first lumen 124A. In the embodiment of FIG. 4, first aperture 128A is disposed on a first side 108A of staple 100. Staple 100 also includes a second side 108B, generally opposite first side 108A.

First claw 130A can be seen extending beyond first aperture 128A by a first distance in FIG. 4A. First claw 130A can be seen extending beyond first aperture 128A by a second distance in FIG. 4B with the second distance greater than the first distance. The position of first claw 130A in FIG. 4A may be referred to as a delivery position and the position of first claw 130A in FIG. 4B may be referred to as a deployed position. When first claw 130A is in the deployed position, a distal portion of first claw 130 extends in a direction that is generally transverse to first longitudinal axis 126A. When first claw 130 extends in a direction transverse to first longitudinal axis 126A first claw 130A may act to retain first trunk 120A in a tissue.

In the embodiment of FIG. 4, first claw 130A comprises a body 133 extending along a curvilinear axis 132. Body 133 of first claw 130A includes an upper surface 138 and lower surface 140 that are separated by the height of body 133. Upper surface 138 of first claw 130A includes a convex surface 142. Lower surface 140 of first claw 130A includes a concave surface 144. In the embodiment of FIG. 4, body 133 has a tapering shape such that the height of body 133 changes along curvilinear axis 132. In FIG. 4B, upper surface 138 of body 150 can be seen contacting a proximal edge surface 146B and lower surface 140 of body 150 can be seen contacting distal edge surface 146A. Proximal edge surface 146B and distal edge surface 146A partially define a first aperture 128A. First aperture 128A is defined by a plurality of edge surfaces of wall 120. More particularly, in the exemplary embodiment of FIG. 4, first aperture 128A is defined by proximal edge surface 146B, distal edge surface 146A, and two side edge surfaces. Only one side edge surface 146D is visible in the cross-sectional view of FIG. 4. The height of first claw 130A is selected so that an interference fit is formed between first claw 130A and first trunk 102A when first claw is disposed in the locked position of FIG. 4B.

In FIG. 4, a first pull member 160A can be seen extending into lumen 124 of first trunk 120A. The first pull member 160A includes a control rod 170 that is slidably disposed in lumen 124 of first trunk 120A. Control rod 170 and first claw 130A engage each other to form a mechanically interlocking but releasable connection 162. Connection 162 is configured such that a proximally directed force applied to control rod 170 is transferred to first claw 130A to urge movement of first claw 130A between the delivery position of FIG. 4A and the deployed position of FIG. 4B. The proximal direction P and a distal direction D are illustrated with arrows in FIG. 4. In the exemplary embodiment of FIG. 4, control rod 170 includes a tab 164 that is received in a notch 166 defined by first claw 130A.

In the embodiment of FIG. 4, the height of body 133 varies along curvilinear axis 132 such that, when first claw 130A reaches the deployed position of FIG. 4B, an intermediate portion of first claw 130A becomes wedged between proximal edge surface 146B and distal edge surface 146A, forming an interference fit between first claw 130A and first trunk 120A. In the embodiment of FIG. 4, the proximally directed force applied to first claw 130A by first pull member 160 is offset from proximal edge 146B such that the proximally directed force causes first claw 130A to rotate as upper surface 138 slides along proximal edge 146B. The proximal end of first claw 130A comprises a knife edge 168. In some useful embodiments, knife edge 168 is sufficiently sharp and made of a material sufficiently hard to cut into at least a portion of the thickness of the material of wall 120. The penetrating engagement between knife edge 168 and wall 120 may help retain first claw 130A in the deployed position shown in FIG. 4B.

Figure 5A:
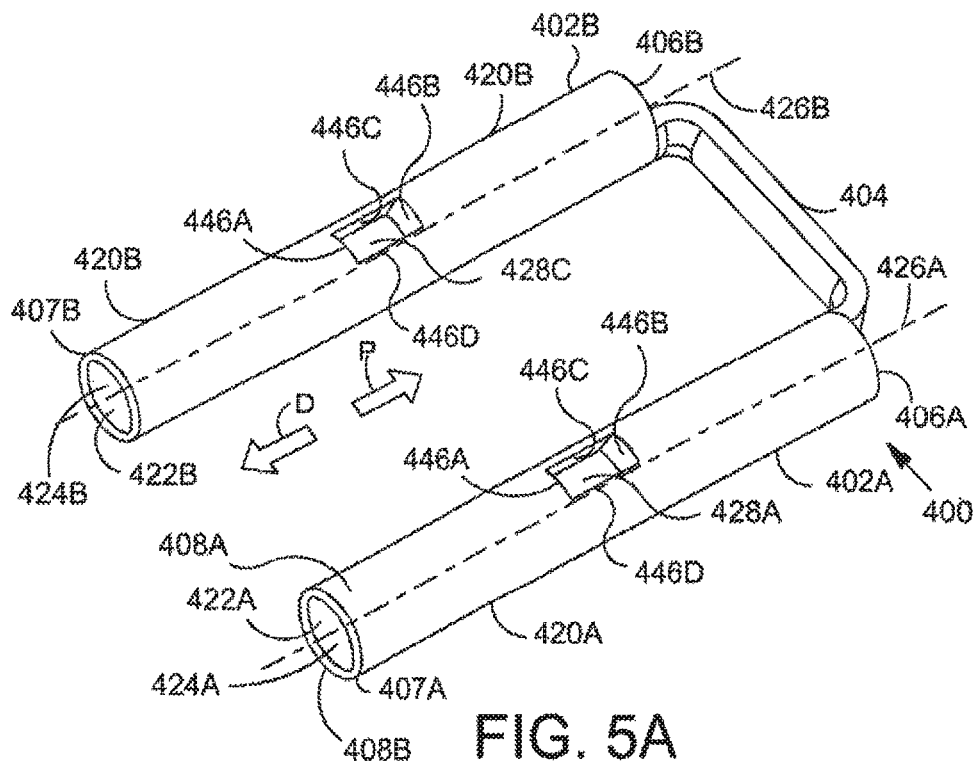
FIGS. 5A-5B are alternative perspective views of another exemplary tissue fastener of the present disclosure.
Figure 5B:
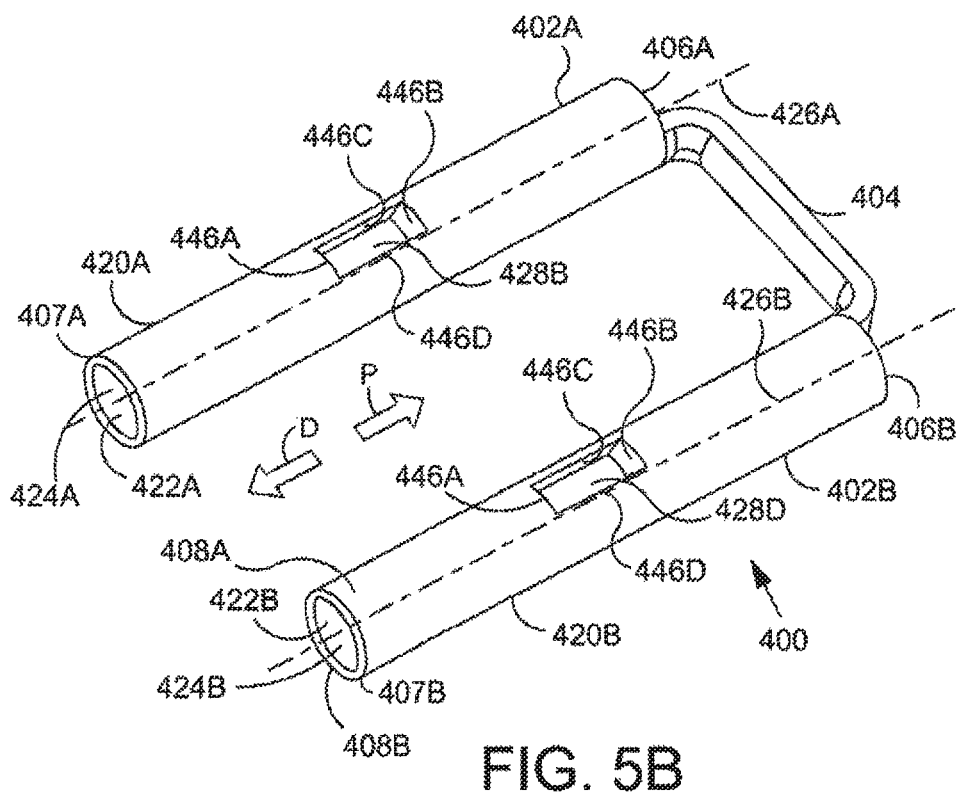

FIG. 5A and FIG. 5B are perspective views illustrating another exemplary staple 400 in accordance with the present detailed description. FIGS. 5A and 5B may be collectively referred to as FIG. 5. With reference to FIG. 5, it will be appreciated that staple 400 may assume various orientations without deviating from the spirit and scope of this detailed description. Reference directions are illustrated using arrows in to identify a proximal direction P and a distal direction D.

Staple 400 of FIG. 5 can included a first arm 402A, a second arm 402B and a bridge 404. First arm 402A has a proximal end 406A and a distal end 407A. Second arm 402B has a proximal end 406B and a distal end 407B. In the embodiment of FIG. 5, a first end of bridge 404 abuts the proximal end 406A of first arm 402A and a second end of bridge 404 abuts the proximal end 406B of second arm 402B. Bridge 404 can be seen extending between proximal end 406A of first arm 402A and proximal end 406B of second arm 402B. In the embodiment of FIG. 5, each arm 402A, 402B include a first trunk 420A and a second trunk 420B, respectively. As illustrated the trunks extend for substantially the entire length of the arms 402A, 402B. However, this length may be varied in alternative embodiments.

In the embodiment of FIG. 5, staple 400 includes a plurality of apertures 428. These apertures 428 include a first aperture 428A, a second aperture 428B, a third aperture 428C, and a fourth aperture 428D. First aperture 428A and second aperture 428B extend through a first wall of first trunk 420A. Third aperture 428C and fourth aperture 428D extend through a second wall of second trunk 420B. Each aperture 328 is defined by a plurality of edge surfaces of the wall defining that aperture. More particularly, in the exemplary embodiment of FIG. 5, each aperture 328 is defined by a proximal edge surface 446B, a distal edge surface 446A, and two side edge surfaces 446C and 446D.

First wall of first trunk 420A has an inner surface 422A defining a first lumen 424A. First lumen 424A extends along a first longitudinal axis 426A. First wall of first trunk 420A also defines first aperture 428A and second aperture 428B. First aperture 428A is disposed on a first side 408A of staple 400 and second aperture 428B is disposed on a second side 408B of staple 400. First aperture 428A and a second aperture 428B both fluidly communicate with first lumen 424A. In FIG. 5, first wall of first trunk 420A is shown assuming a relaxed shape in which no external forces are acting on the first wall. With reference to FIG. 5, it will be appreciated that the relaxed shape of the first wall has a generally circular profile in a plane orthogonal to first longitudinal axis 426A when the first wall is free to assume the relaxed shape.

Second wall of second trunk 420B has an inner surface 422B that defines a first lumen 424A. Second lumen 424B extends along a second longitudinal axis 426B. Second wall 420B of second trunk 402B also defines third aperture 428C and fourth aperture 428D. Third aperture 428C and a fourth aperture 428D both fluidly communicate with first lumen 424A. Third aperture 428C is disposed on first side 408A of staple 400 and second aperture 428B is disposed on second side 408B of staple 400. In FIG. 5, the second wall of second trunk 420B is shown assuming a relaxed shape in which no external forces are acting on the second wall. As discussed above, the second wall has a generally circular profile in a plane orthogonal to second longitudinal axis 426B when second wall is free to assume the relaxed shape.

Figure 6A:
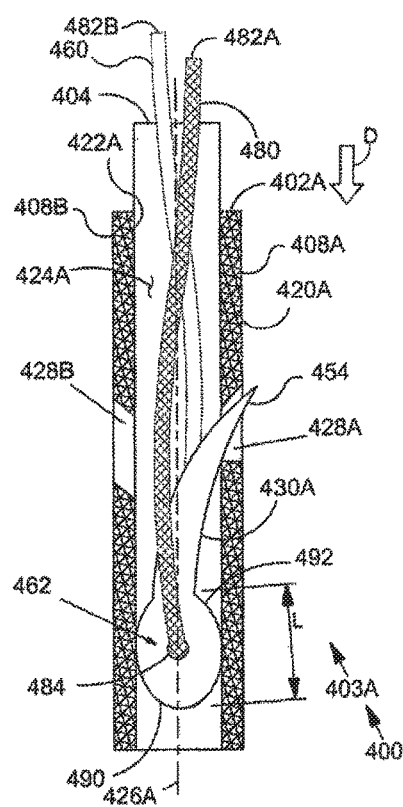
FIGS. 6A-6B are partial cross sectional views of the fastener of FIGS. 5A-5B depicting a projection in a first retracted state and a second deployed or extended state, respectively.
Figure 6B:
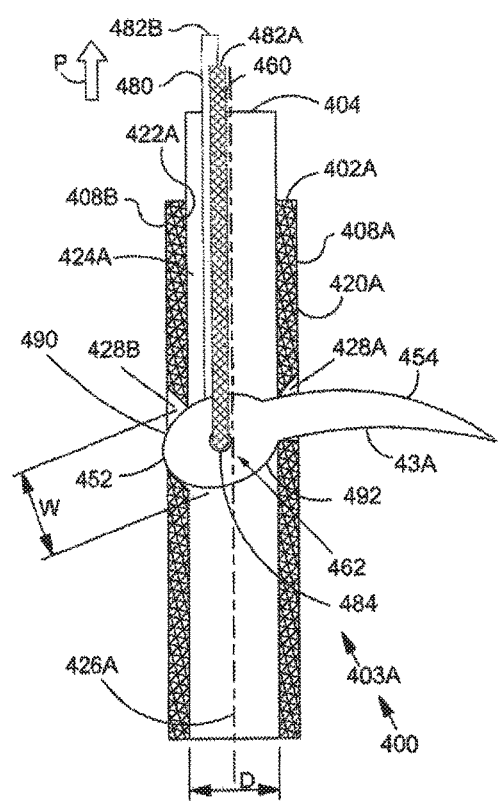

FIG. 6A and FIG. 6B are cross-sectional views illustrating the internal portion of the trunk 420A of a staple 400 as described above. The trunk 420 includes a trunk assembly 403A which mechanism acts to retain the staple in tissue. The first trunk assembly 403A includes a first claw 430A that is partially disposed in a first lumen 424A defined by a first trunk 420A. First claw 430A is disposed in a delivery position in the embodiment of FIG. 6A. In the embodiment of FIG. 6B, however, first claw 430A is disposed in a deployed position. First claw 430A is disposed in the delivery position of FIG. 6A when first trunk assembly 403A is in a delivery configuration. First claw 430A is disposed in the deployed position of FIG. 6B when first trunk assembly 403A is in a deployed configuration. In the exemplary embodiment of FIG. 6, first trunk assembly 403A is configured to transition between and be stable in only the delivery configuration of FIG. 6A and the deployed configuration of FIG. 6B.

First trunk 420A of staple 400 includes a first wall having a first inner surface 422A defining a first lumen 424A. In the embodiment of FIG. 6, first lumen 424A extends along a first longitudinal axis 426A. A diameter D of first lumen 424A is illustrated using dimension lines in FIG. 6B. The first wall of first trunk 402A defines first aperture 428A and second aperture 428B in the embodiment of FIG. 6. In some embodiments, a center of first aperture 428A and a center of second aperture 428B are generally aligned with each other along opposite sides of longitudinal axis 426A. First aperture 428A is disposed on a first side 408A of staple 400 and second aperture 428B is disposed on a second side 408B of staple 400. With reference to FIG. 6, it will be appreciated that first side 408A and second side 408B are opposite sides. First aperture 428A and a second aperture 428B both fluidly communicate with first lumen 424A.

First claw 430A can be seen extending beyond first aperture 428A by a first distance in FIG. 6A. First claw 430A can be seen extending beyond first aperture 428A by a second distance in FIG. 6B. With reference to FIG. 6, it will be appreciated that the second distance is greater than the first distance. The position of first claw 430A in FIG. 6A may be referred to as a delivery position of first claw 430A and in FIG. 6B may be referred to as a deployed position. When first claw 430A is in the deployed position, a distal portion of first claw 430A extends in a direction that is generally transverse to first longitudinal axis 426A. When first claw 430A extends in a direction transverse to first longitudinal axis 426A first claw 430A may act to retain first trunk 420 in a tissue.

In the embodiment of FIG. 6, first claw 430A comprises a head 452 including an anterior edge 490 opposite a posterior edge 492. A tail 454 of first claw 430A abuts posterior edge 492 of head 452. The first wall of first trunk 420A is shown assuming a relaxed shape in which no external forces are acting on the first wall. In the exemplary embodiment of FIG. 6, the relaxed shape of the first wall has a generally circular profile in a plane orthogonal to first longitudinal axis 426A when the first wall is free to assume the relaxed shape. In the embodiment of FIG. 6, head 452 is shaped and dimensioned such that camming forces applied to the first wall of first trunk 420A by anterior edge 490 of head 452 as first claw 430A moves between the delivery position of FIG. 6A and the deployed position of FIG. 6B will urge a portion of the first wall toward an elastically deflected shape that is more elliptical than the relaxed shape of the wall. The material of the first wall can have a level of elasticity such that the first wall returns to the relaxed shape when first claw 430A reaches the deployed position of FIG. 6B. The plurality of edge surfaces that define first aperture 428A and second aperture 428B create a physical barrier preventing first claw 430A from moving out of the deployed position.

With reference to FIG. 6B, it will be appreciated that, when first claw 430A is disposed in the deployed position, first claw 430A extends across first lumen 424A with anterior edge 490 extending into second aperture 428B and tail 454 extending through first aperture 428A. With reference to FIG. 6A, it will be appreciated that, when first claw 430A is disposed in the delivery position, head 452 of first claw 430A is disposed completely within first lumen 424A.

In FIG. 6, a pull member 460 can be seen extending into first lumen 424A of first trunk 420A. Pull member 460 can include a suture 480 having a first end 482A and a second end 482B. Suture 480 and first claw 430A engage each other to form a connection 462. Connection 462 is configured such that a proximally directed force applied to suture 480 is transferred to first claw 430A to urge movement of first claw 430A between the delivery position of FIG. 6A and the deployed position of FIG. 6B. The proximal direction P and a distal direction D are illustrated with arrows in FIG. 6. In the exemplary embodiment of FIG. 6, first claw 430A defines a hole 484. A portion of suture 480 extending between first end 482A and second end 482B is threaded through hole 484 defined by first claw 430.

Methods in accordance with this detailed description may include the step of moving a claw from a delivery position (e.g., the delivery position of FIG. 6A) to a deployed position (e.g., the deployed position of FIG. 6B). In the embodiment of FIG. 6, first claw 430A can be moved from the delivery position of FIG. 6A to the deployed position of FIG. 6B by applying a proximally directed pulling force on first end 482A and second end 482B of suture 480. After first claw 430A has been deployed, suture 480 may be removed by pulling one of first end 482A and second end 482B through hole 484 defined by first claw 430A.

Figure 7A:
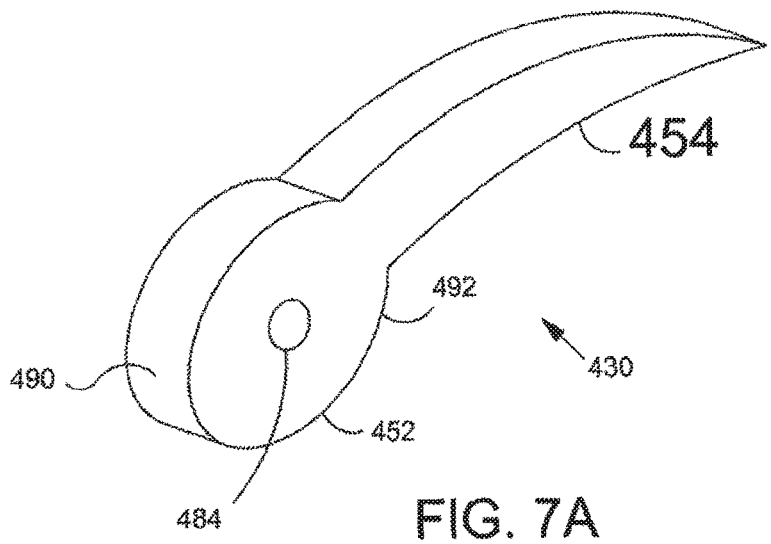
FIGS. 7A-7B are alternative views of a tissue retention member in accordance with the present disclosure.
Figure 7B:
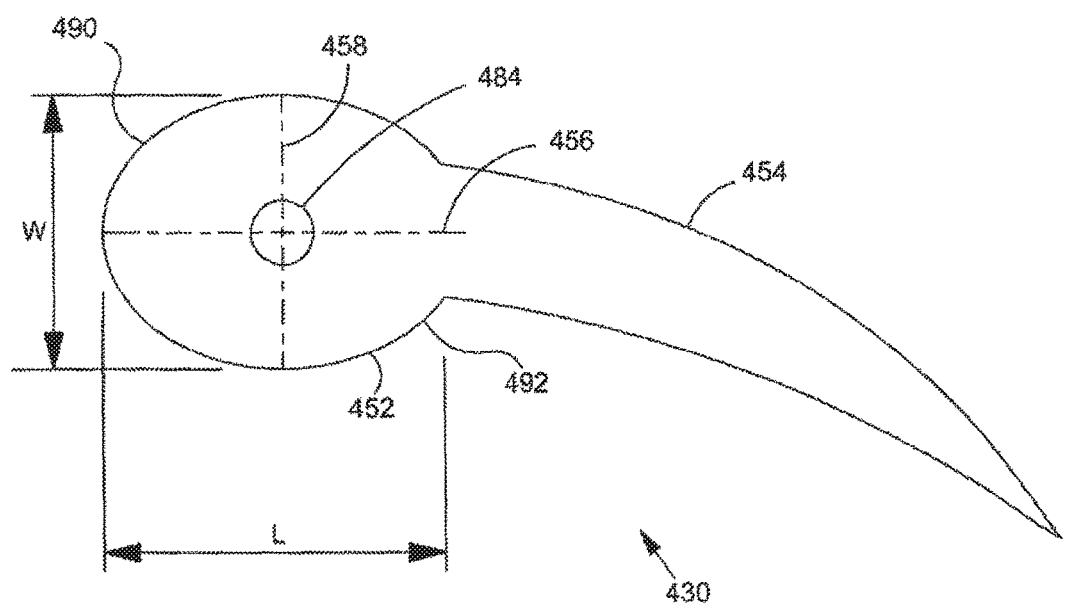

FIG. 7A is a perspective view of an exemplary claw 430 in accordance with this detailed description. FIG. 7B is a plan view of claw 430 shown in FIG. 7A. FIG. 7A and FIG. 7B may be collectively referred to as FIG. 7. In the embodiment of FIG. 7, claw 430 comprises a head 452 including an anterior edge 490 opposite a posterior edge 492. A tail 454 of claw 430 abuts posterior edge 492 of head 452 in the embodiment of FIG. 7. Head 452 of claw 430 defines a hole 484. Head 452 is shaped and dimensioned such that camming forces applied to a wall (e.g., first wall shown in FIG. 6) by anterior edge 490 of head 452 as claw 430 moves between a delivery position and a deployed position will urge a portion of the wall toward an elastically deflected shape that is more elliptical than the relaxed shape of the wall. Head 450 of claw 430 has a major axis 456 and a minor axis 458. As illustrated in FIG. 7B, head 450 has a length L measured in a direction generally parallel to major axis 456. A width W of head 450 is also illustrated in FIG. 7B. With reference to FIG. 7B, it will be appreciated that width W is measured in a direction that is generally parallel to minor axis 458. In the exemplary embodiment of FIG. 7, length L is greater than width W.

Referring again to FIG. 6, it will be appreciated that width W of head 652 is less than or about equal to the diameter D of first lumen 424A. In the embodiment of FIG. 6, length L of head 450 is greater than the diameter D of first lumen 424A. With reference to FIG. 6A, it will be appreciated that the major axis of head 452 is generally parallel to first longitudinal axis 426A of first lumen 424A when first claw 430A is in the delivery position. The minor axis of head 452 extends in a direction transverse to first longitudinal axis 426A of first lumen 424A when first claw 430A is in the delivery position of FIG. 6A. With reference to FIG. 6B, it will be appreciated that the major axis of head 452 is generally transverse to first longitudinal axis 426A of first lumen 424A when first claw 430A is in the deployed position. The minor axis of head 452 extends in a direction generally parallel to first longitudinal axis 426A of first lumen 424A when first claw 430A is in the deployed position of FIG. 6B.

Figure 8A:
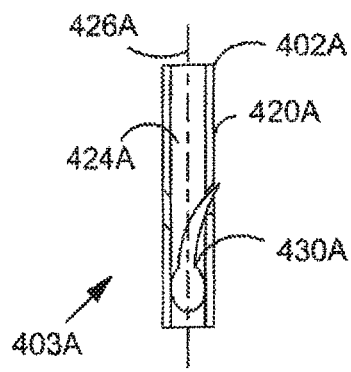
FIGS. 8A-8F are a combination of partial cross sectional views and partial top views depicting the deployment of a tissue retention member.
Figure 8D:
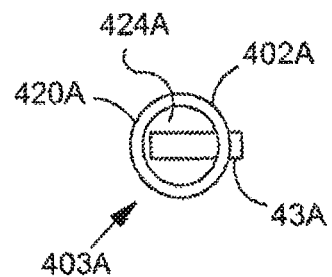
Figure 8B:
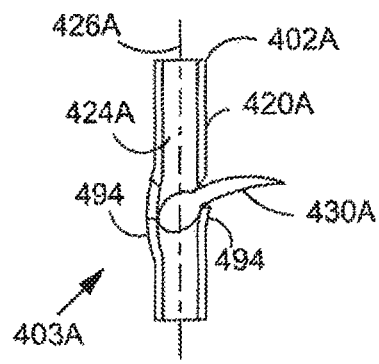
Figure 8E:
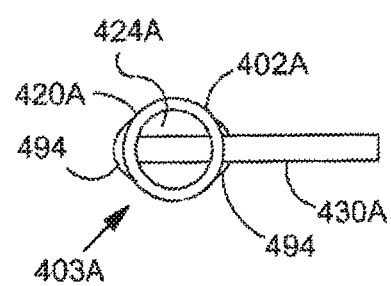
Figure 8C:
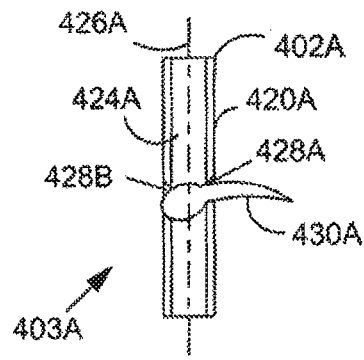
Figure 8F:
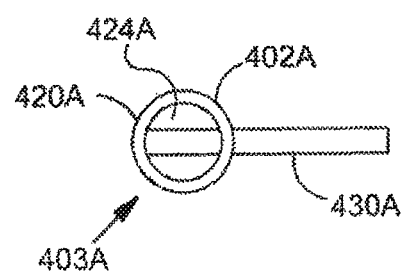

FIG. 8A, FIG. 8B and FIG. 8C form a sequence of stylized front plan views illustrating an exemplary method in accordance with this detailed description. FIG. 8D, FIG. 8E and FIG. 8F form a sequence stylized top plan views further illustrating the method shown in FIG. 8A, FIG. 8B and FIG. 8C.

FIG. 8A and FIG. 8D are plan views showing a first trunk assembly 403A. In the exemplary embodiment of FIG. 8A and FIG. 8D, first trunk assembly 403A is in a delivery configuration. First trunk assembly 403A includes a first claw 430A that is partially disposed in a first lumen 424A defined by a first wall 420A of a first trunk 402A. First lumen 424A extends along a first longitudinal axis 426A. First claw 430A is disposed in a delivery position in the embodiment of FIG. 8A and FIG. 8D. With reference to FIG. 8A, it will be appreciated that a head of first claw 430A is disposed completely within lumen 424A when first claw 430A is in the delivery position. In FIG. 8A and FIG. 8D, first wall of first trunk 302A is shown assuming a relaxed shape in which no external forces are acting on first wall. With reference to FIG. 8D, it will be appreciated that the relaxed shape of first trunk 420A has a generally circular profile in a plane orthogonal to first longitudinal axis 426A when first wall of the first trunk 420A is free to assume the relaxed shape.

FIG. 8B and FIG. 8E are additional plan views showing first trunk assembly 403A. In the exemplary embodiment of FIG. 8B and FIG. 8E, first trunk assembly 403A is in the process of transitioning between the delivery configuration of FIG. 8A and a deployed configuration. The deployed configuration is illustrated in FIG. 8C and FIG. 8F. In the embodiment of FIG. 8B, a head of first claw 430A is shaped and dimensioned such that camming forces applied to first wall of first trunk 420A by an anterior edge of first claw 430A as the first claw moves between the delivery position of FIG. 8A and the deployed position of FIG. 8C will urge a portion of first wall 420A toward an elastically deflected shape that is more elliptical than the relaxed shape of the wall. In the exemplary embodiment of FIG. 8, the material of first trunk 420A has a level of elasticity such that first wall returns to the relaxed shape when first claw 430A reaches the deployed position of FIG. 8C. In the embodiment of FIG. 8B and FIG. 8E, the camming forces acting on first wall have produced bulges 494 in first trunk 420A.

FIG. 8C and FIG. 8F are plan views showing first trunk assembly 403A in a deployed configuration. First trunk assembly 403A includes a first claw 430A that is partially disposed in a first lumen 424A defined by a first trunk 402A. First claw 430A is disposed in a deployed position in the embodiment of FIG. 8C and FIG. 8F. In FIG. 8F, a first wall of first trunk 420A is shown assuming a relaxed shape in which no external forces are acting on first wall of first trunk 420A. In the exemplary embodiment of FIG. 8F, the relaxed shape of first wall of first trunk 420A has a generally circular profile in a plane orthogonal to first longitudinal axis 426A when first wall 420A is free to assume the relaxed shape.

In FIG. 8C, a tail portion of first claw 430A can be seen extending through a first aperture 428A defined by first wall of first trunk 420A. An anterior edge of the head portion of first claw 430A can be seen extending into a second aperture 428B defined by first wall of first trunk 420A in FIG. 8C. In the embodiment of FIG. 8C, the plurality of edge surfaces defining the apertures create a physical barrier preventing first claw 430A from moving out of the deployed position.

Figure 9A:
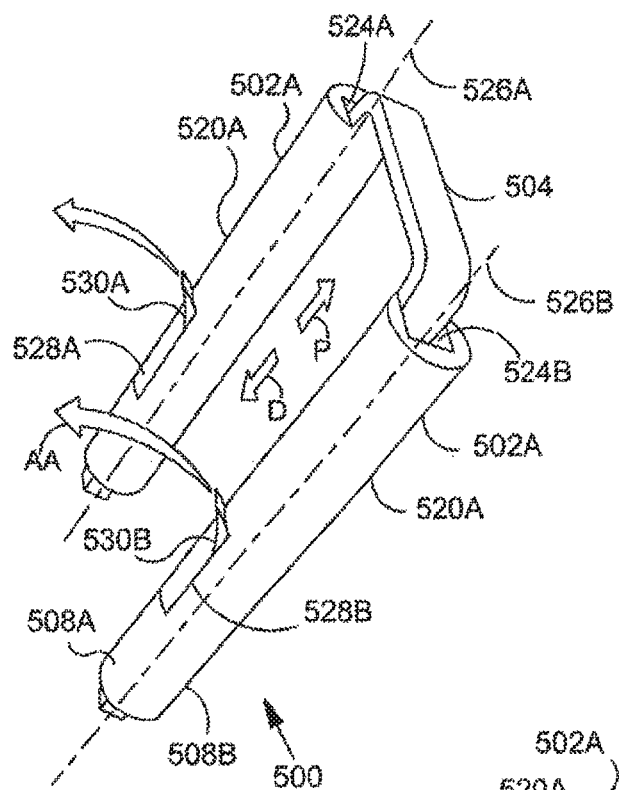
FIGS. 9A-9B are perspective views of a tissue fastener having a tissue retention member in a retracted and a deployed position.
Figure 9B:
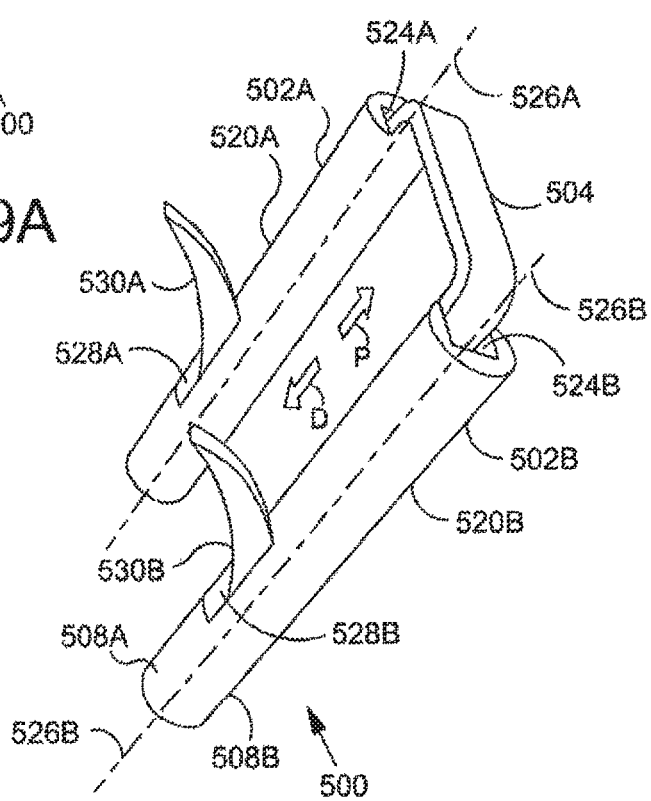

FIGS. 9A and 9B provide perspective views of a staple 500 of the present disclosure. Each staple can include a first and second arm 502A, 502B, each having a proximal end attached to a bridge 504 extending therebetween. Each arm includes a trunk 520A, 520B, generally of larger cross section than the bridge 504. In some embodiments, the trunk 520 extends the entire length of the arm 502 and has a proximal end fixed to the bridge 504. Alternatively, the arms can include a trunk and non-trunk portion, with the non-trunk portion extending between the proximal end of the trunk and the bridge.

Each trunk 520 has a lumen or cavity 524 therein in which is disposed a claw 530. Each trunk further includes at least one aperture 528 through a side wall thereof. The claw 530 is sized and shaped to fit within the lumen or cavity 524 and move between a first retracted or delivery position (FIG. 9A) and a second extended or deployed position (FIG. 9B) wherein at least a portion of the claw 530 interacts with bone to retain the staple 500 in position at a treatment site.

Figure 10:
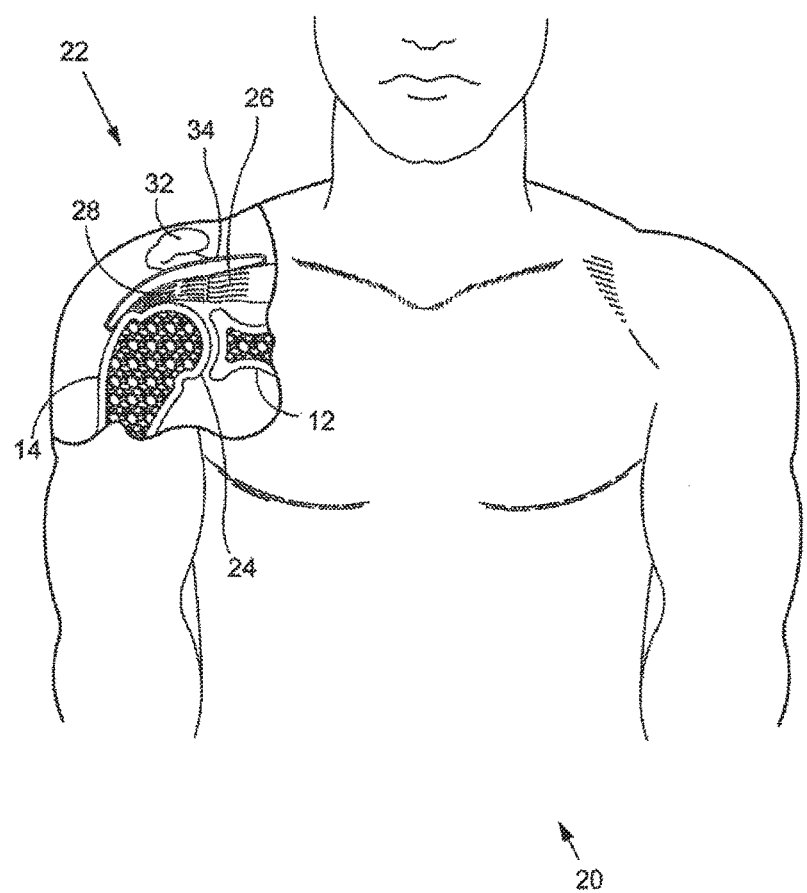
FIG. 10 is a stylized anterior view of a shoulder including a humerus and a scapula.

Next referring to FIG. 10, an exemplary use or application of the staples of the present disclosure is described. FIG. 10 is a stylized anterior view of a patient 20. For purposes of illustration, a shoulder 22 of patient 20 is shown in cross-section in FIG. 10. Shoulder 22 includes a humerus 14 and a scapula 12. In FIG. 10, a head 24 of humerus 14 can be seen mating with a glenoid fossa of scapula 12 at a glenohumeral joint. With reference to FIG. 10, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 10.

With reference to FIG. 10, a distal tendon 28 of the supraspinatus 26 meets humerus 14 at an insertion point. Scapula 12 of shoulder 22 includes an acromium 32. In FIG. 10, a subacromial bursa 34 is shown extending between acromium 32 of scapula 12 and head 24 of humerus 14. Subacromial bursa 34 is shown overlaying supraspinatus 26 as well as supraspinatus tendon 28 and a portion of humerus 14. Subacromial bursa 34 is one of the hundreds of bursae found the human body. Each bursa comprises a fluid filled sac. The presence of these bursae in the body reduces friction between bodily tissues.

The exemplary staples or fasteners described herein may be used to affix tendon repair implants to various target tissues. The shoulder depicted in FIG. 10 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 11:
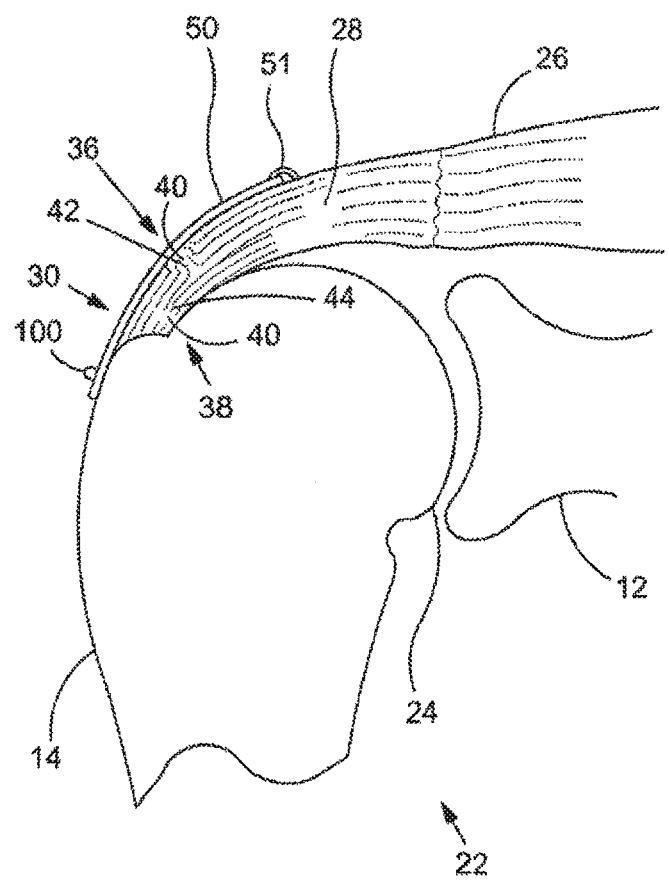
FIG. 11 is a stylized of a shoulder depicting the head of the humerus shown mating with the glenoid fossa of the scapula at a glenohumeral joint and a sheet-like material is affixed to the tendon.

FIG. 11 is a stylized anterior view of a shoulder 22 including a humerus 14 and a scapula 12. In FIG. 11, a head 24 of humerus 14 is shown mating with a glenoid fossa of scapula 12 at a glenohumeral joint. A supraspinatus 26 is also shown in FIG. 11. This muscle, along with others, controls the movement of humerus 14 relative to scapula 12. A distal tendon 28 of supraspinatus 26 meets humerus 14 at an insertion point 30.

As depicted in FIG. 11, distal tendon 28 includes a first damaged portion 36. A number of loose tendon fibers 40 in first damaged portion 36 are visible in FIG. 11. First damaged portion 36 includes a first tear 42 extending partially through distal tendon 28. First tear 42 may therefore be referred to as a partial thickness tear. With reference to FIG. 11, first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 11, distal tendon 28 includes a second damaged portion 38 located near insertion point 30. As illustrated, second damaged portion 38 of distal tendon 28 has become frayed and a number of loose tendon fibers 40 are visible. Second damaged portion 38 of distal tendon 28 includes second tear 44. Second tear 44 begins on the side of distal tendon 28 facing the center of the humeral head 24. Accordingly, second damaged portion 38 may be referred to as an articular side tear.

FIG. 11 illustrates a sheet-like implant 50 has been placed over the bursal side of distal tendon 28. The sheet-like implant 50 is affixed to distal tendon 28 by a plurality of tendon staples 51. Sheet-like implant 50 is affixed to humerus 14 by a plurality of bone staples 100 in accordance with designs of staples disclosed herein. Sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon.

Figure 12:
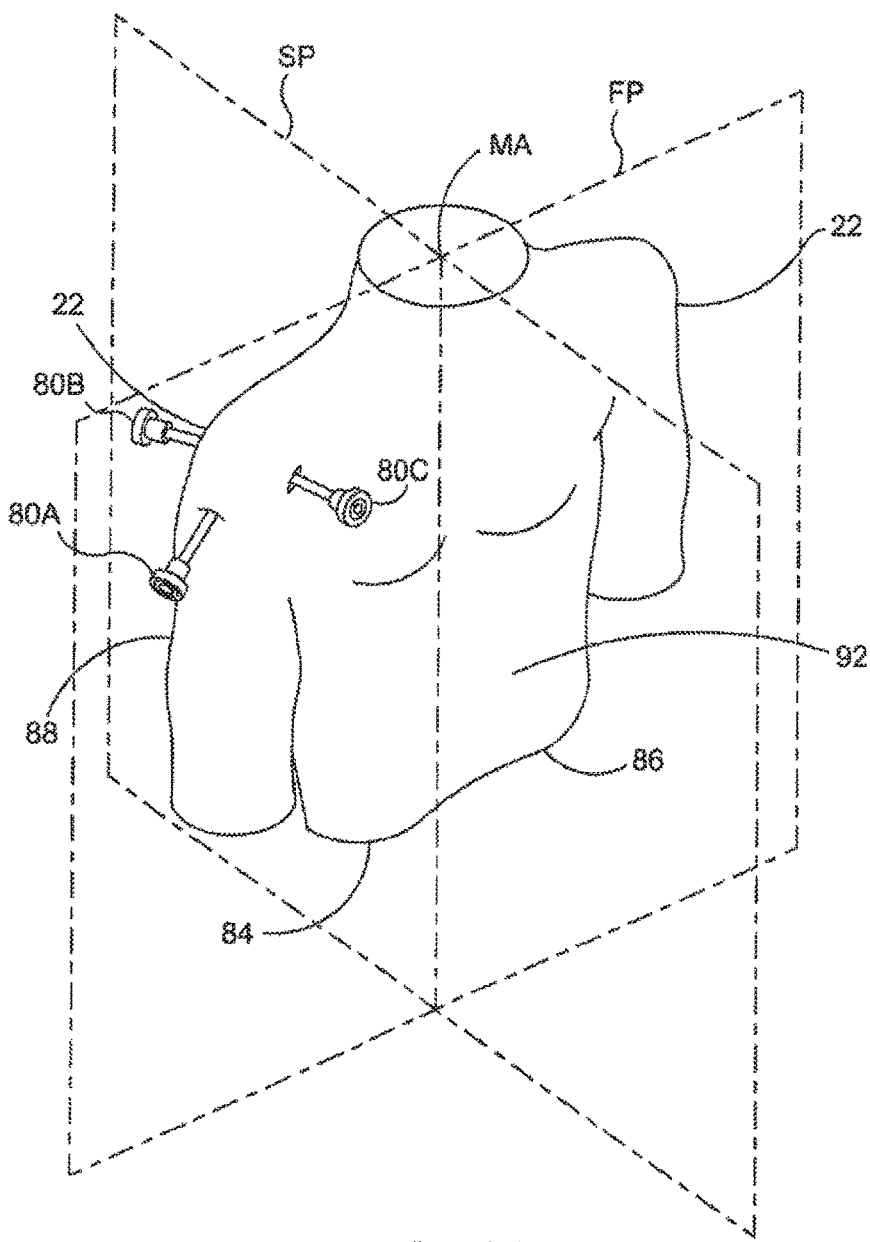
FIG. 12 is a stylized perspective view showing a portion of the body of a human patient divided into quadrants by planes for descriptive purposes herein.

FIG. 12 is a stylized perspective view showing a portion of the body 82 of a human patient 20. Body 82 includes a shoulder 22. In the exemplary embodiment of FIG. 12, a plurality of cannulas are positioned to access a treatment site within shoulder 22. In some cases, shoulder 22 may be inflated by pumping a continuous flow of saline through shoulder 22 to create a cavity proximate the treatment site. The cannulas shown in FIG. 12 include a first cannula 80A, a second cannula 80B and a third cannula 80C.

In FIG. 12, a sagital plane SP and a frontal plane FP are shown intersecting body 82. Sagital plane SP and frontal plane FP intersect one another at a medial axis MA of body 82. With reference to FIG. 12, sagital plane SP bisects body 82 into a right side 84 and a left side 86. Also with reference to FIG. 12, frontal plane FP divides body 82 into an anterior portion 92 and a posterior portion 88. Sagital plane SP and a frontal plane FP are generally perpendicular to one another. These planes and portions are used to describe the procedures used in exemplary embodiments.

First cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. Second cannula 80B is accessing a treatment site within shoulder 22 using a posterior approach in which second cannula 80B pierces the outer surface of posterior portion 88 of body 82. Third cannula 80C is accessing a treatment site within shoulder 22 using an anterior approach in which third cannula 80C pierces the outer surface of anterior portion 92 of body 82.

Figure 13:
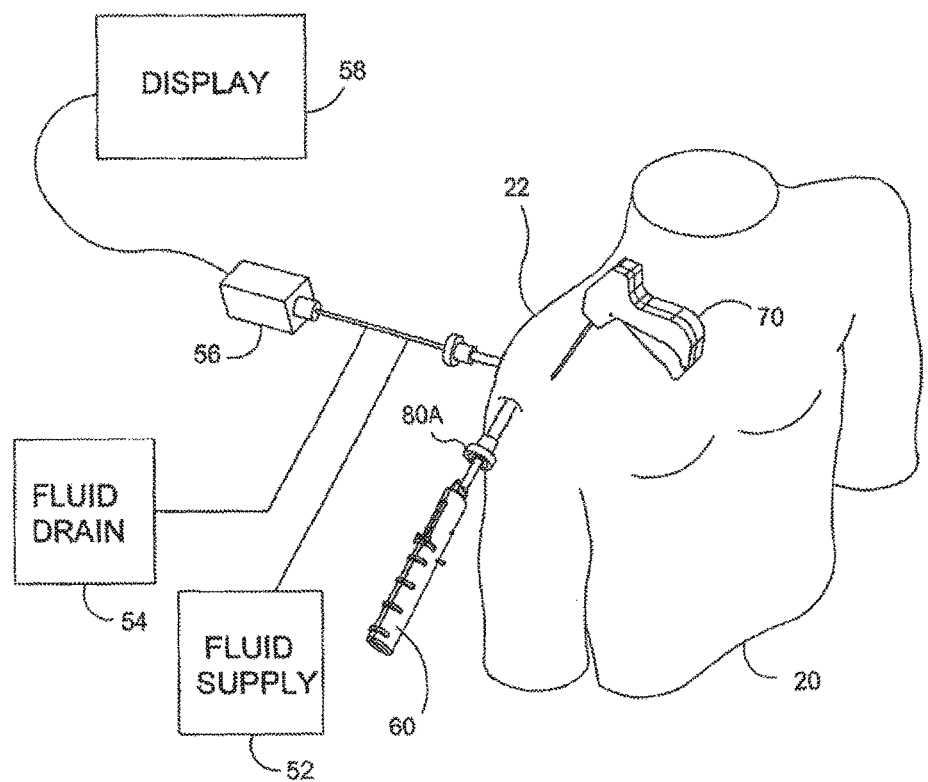
FIG. 13 is a stylized perspective view illustrating an exemplary procedure for arthroscopic treatment of a shoulder of a patient in accordance with one embodiment of the disclosure.

FIG. 13 is a stylized perspective view illustrating an exemplary procedure for treating a shoulder 22 of a patient 20. The procedure illustrated in FIG. 13 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 13 has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

An implant delivery system 60 can be seen extending from shoulder 22 in FIG. 13. Implant delivery system 60 is extending through a first cannula 80A. In certain embodiments, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. When that is the case, the implant delivery system may be advanced through tissue. Implant delivery system 60 comprises a sheath that is affixed to a handle. The sheath defines a lumen and a distal opening fluidly communicating with the lumen. In the embodiment of FIG. 13, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some embodiments, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the exemplary embodiment of FIG. 13, the shaft of a fixation tool 70 is shown extending into shoulder 22. In one exemplary embodiment, fixation tool 70 is capable of fixing the tendon repair implant to the tendon and bone with one or more staples of the present disclosure while the tendon repair implant may held against the tendon by implant delivery system 60.

Figure 14:
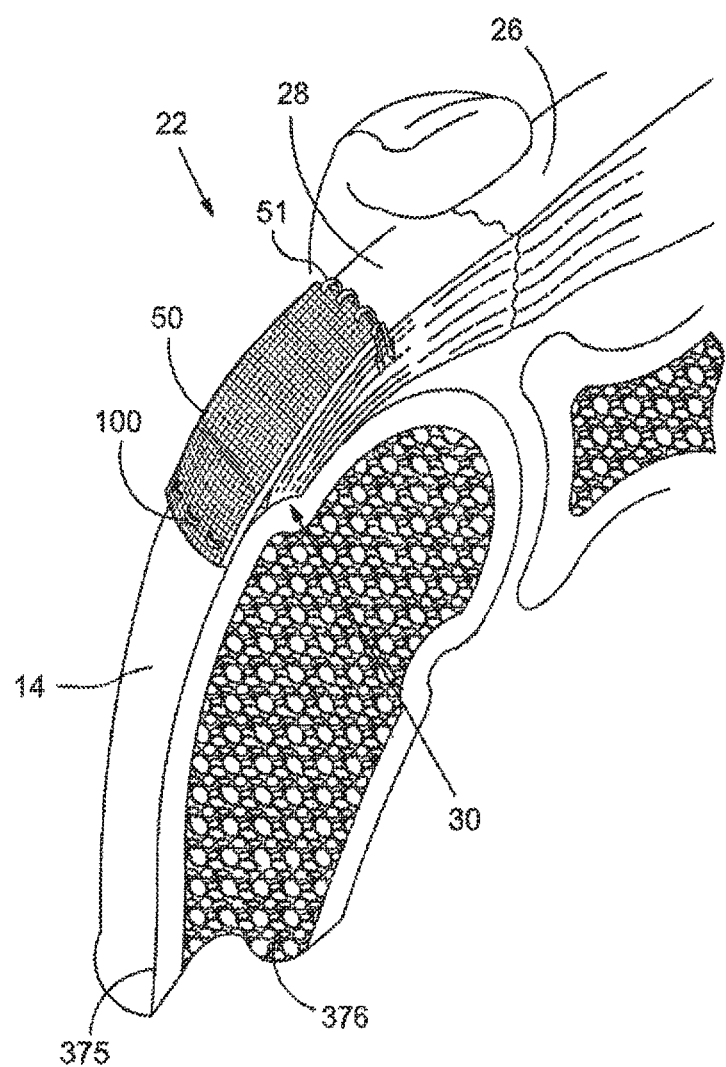
FIG. 14 is a stylized perspective view of a shoulder including a supraspinatus having a distal tendon with a sheet-like material affixed thereto.

FIG. 14 is a stylized perspective view of a shoulder 22 including a supraspinatus 26 having a distal tendon 28. With reference to FIG. 14, a tendon repair implant 50 has been affixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiments, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIOMATERIAL™. The sheet-like structure may be circular, oval, oblong, square, rectangular, or other shape configured to suit the target anatomy.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the embodiment of FIG. 14, sheet-like implant 50 is affixed to distal tendon 28 by a plurality of tendon staples 51. Sheet-like implant 50 is affixed to humerus 14 by a plurality of bone staples 100 as described with respect to the exemplary embodiment of FIG. 1 and detailed throughout this disclosure.

In some exemplary methods, a plurality of staples may be applied using a fixation tool. After the staples are applied, the fixation tool may be withdrawn from the body of the patient. Distal tendon 28 meets humerus 14 at an insertion point 30. With reference to FIG. 14, it will be appreciated that sheet-like implant 50 extends over insertion point 30. Tendon repair implant may be applied to distal tendon 28, for example, using the procedure illustrated in the previous Figures. In various embodiments, staples may straddle the perimeter edge of the sheet-like implant (as shown in FIG. 14), may be applied adjacent to the perimeter, and/or be applied to a central region of the implant. In some embodiments, the staples may be used to attach the implant to soft tissue and/or to bone.

Staples or fasteners 100, as exemplified in FIG. 1 and described and illustrated herein can be used to attach tissue and implants to bone. In at least some embodiments, the staple is generally flexible. With this flexibility, the fasteners cannot be pounded or driven into bone or other tissue as a conventional hard staple would be driven into paper, wood, tissue or bone. Therefore, for application of the staple of the present disclosure to affixing tissue or implants to bone, the staple is generally included in a kit that also includes a staple delivery device 200 and a pilot hole forming trocar assembly 300, as schematically illustrated in FIGS. 15A and 15B, respectively.

In general, the staple delivery device 200 can include a handle assembly 201 and a barrel assembly 205. The handle assembly 201 includes a trigger 203 that is operatively coupled to mechanisms in the barrel assembly 205 to deploy a staple of the present disclosure in bone. The staple delivery device 200 can be used in conjunction with the pilot hole forming trocar assembly 300 of FIG. 15B.

Figure 15B:
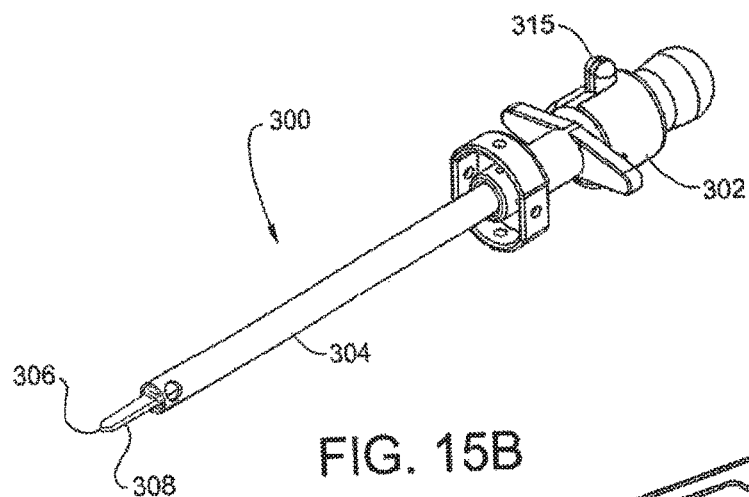
FIG. 15B is a simplified perspective view of a trocar assembly, including a trocar disposed within a guide sheath assembly for creating pilot holes and retaining the sheath within the formed pilot holes for delivery of a tissue fastener or staple by a device such as that depicted in FIG. 10A.
Figure 15A:
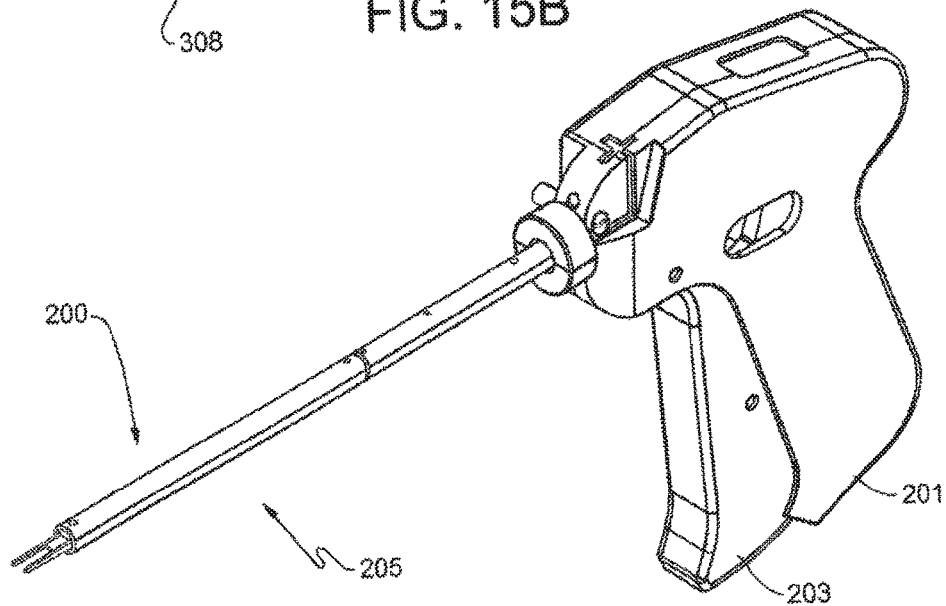
FIG. 15A is a simplified perspective view of a tissue fastener or staple delivery device in accordance with the present disclosure.

The exemplary pilot hole forming trocar assembly 300, illustrated generally in FIG. 15B, includes a trocar 302 and a position retention sleeve 304. The trocar 302 is releasably coupled to the position retention sleeve 304 and slides in keyed arrangement within the sleeve 304 when uncoupled. The trocar 302 includes a distal portion having a retractable blade 306 and a pair of pilot hole forming spikes 308 extending distally from the trocar shaft. The retractable blade 306 is useful in inserting the assembly through an incision. The retractable blade 306 can be retracted by activating release button 315 which causes a spring (not shown) to pull the retractable blade 306 into the shaft of the trocar within the position retention sleeve 304. In this the position, the pilot hole forming spikes remain extended from the shaft. In some embodiments the retractable blade 306 can be omitted, such as when the pilot hole forming trocar assembly is to be inserted into an incision that already has a cannula extending therethrough to provide an instrument path.

Figure 16A:
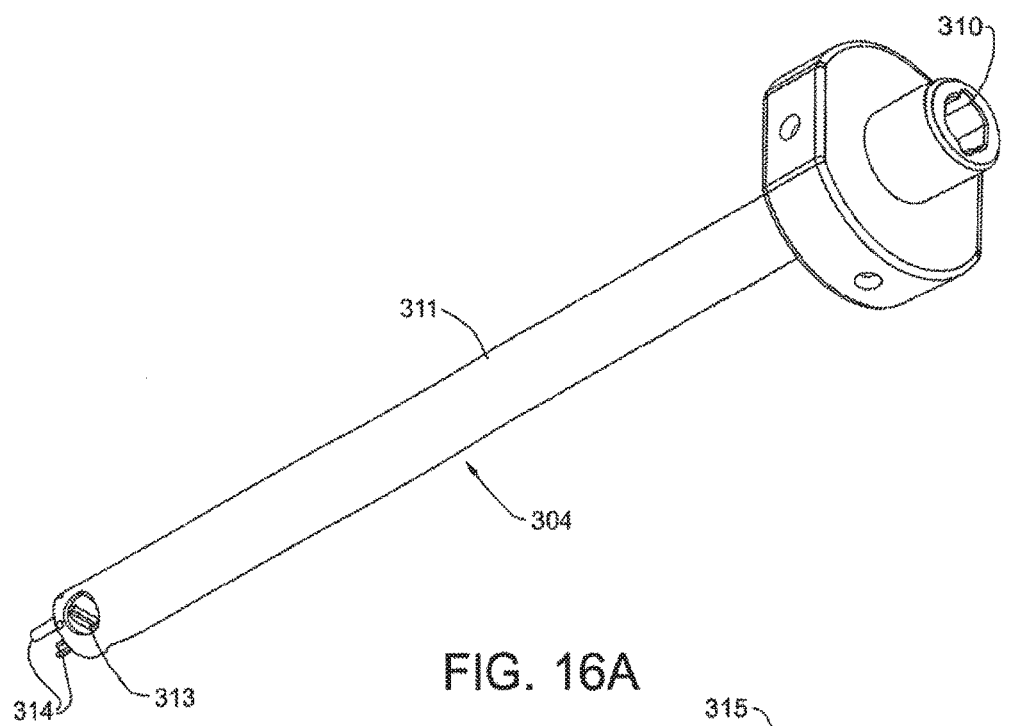
FIG. 16A is a perspective view of the sheath assembly of FIG. 15B with the trocar removed.
Figure 16B:
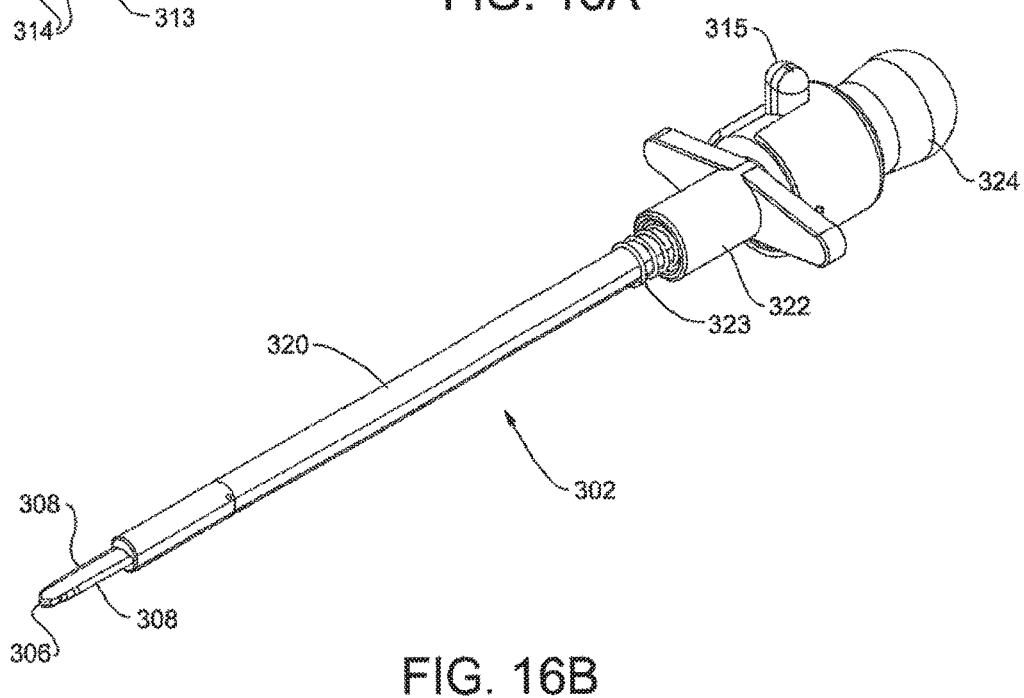
FIG. 16B is a perspective view of the trocar of FIG. 15B as removed from the sheath assembly.
Figure 16C:
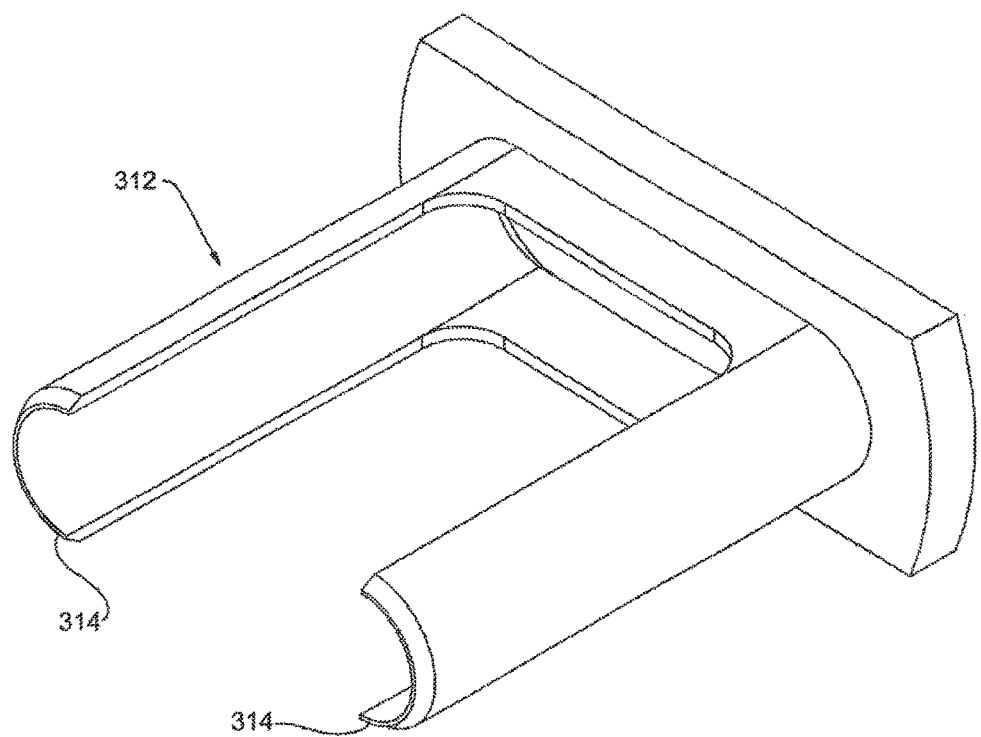
FIG. 16C is a perspective view of one pilot hole position retention member which is positioned in a distal portion of the sheath assembly in one embodiment of the present disclosure.

Referring to FIGS. 16A-16C, details of the elements of one exemplary embodiment of a pilot hole forming trocar assembly 300 are illustrated. The pilot hole forming trocar assembly is used to create pilot holes in a bone for subsequent placement of a staple or fastener, such as staple 100 of FIG. 1. Further, the pilot hole forming trocar assembly includes a means for retaining instrument position with respect to the pilot holes when the trocar is removed so that a staple delivery device 200 can be inserted and the staple be in alignment with the already formed pilot holes. This prevents the time and difficulty associated with finding the pilot holes with the staple, which in fact may not be possible for many practitioners.

As previously stated, a pilot hole forming trocar assembly 300 can include a trocar 302 and a position retention sleeve 304. One embodiment of a position retention sleeve 304 is illustrated in FIG. 16A. The position retention sleeve 304 includes a shaft 311 having a lumen 310 extending therethrough. The lumen 310 is sized to receive the trocar 302 when used to form pilot holes. The lumen 310 is also sized to receive a staple delivery device 200 when used to position a staple in pilot hole formed in bone. The lumen is shaped or keyed to cooperate with either of these instruments or other instruments so that relative rotational position of the trocar 302 or staple delivery device 200 is fixed when slidably positioned in the position retention sleeve. An opening or window 313 may be included near the distal end of the position retention sleeve to allow viewing of devices inserted therein.

Position retention members 314 extend distally from the shaft 311. As detailed in FIG. 16C, the position retention members can be included on an insert 312 that is affixed proximate the distal end of the shaft 311. Alternatively, the position retention members can be integral to the shaft 311. The position retention members are sized and designed to extend into pilot holes as they are formed by the trocar 302 described below. When the trocar 302 is removed, the position retention members 314, along with the sleeve 311 remain in position to provide a guide for the staple delivery device 200 to be inserted into proper position and position a staple 100 in the pilot holes. As depicted, the position retention members 314 can include longitudinally extending semi-cylindrical projections. In the disclosed embodiment, the pilot hole forming spikes 308 of the trocar 302 slide within the partial lumens of the position retention members 314. This design can provide support for the spikes as they are pounded into bone and can also allow the position retention members to readily slide into pilot holes formed by the spikes 308.

A more detailed depiction of another exemplary embodiment of a trocar 302 is included in FIG. 16B. The trocar includes a shaft 320 having at its proximal end a knob 324 that can be used to pound or push the trocar 302 into bone. The trocar can further include a collar 322 which can be used to releasably engage the position retention sleeve 304 when the two are mated for forming pilot holes. A spring 323 can be included which causes or aids the retraction of the trocar when it is released from the position retention sleeve.

As previously disclosed, the distal end of the trocar 302 includes two pilot hole forming spikes 308 extending from shaft 320. A retractable blade 306 is positioned between the spikes 308. In use, the blade 306 is retracted prior to the spikes 308 being used to form pilot holes in bone.

Figure 17A:
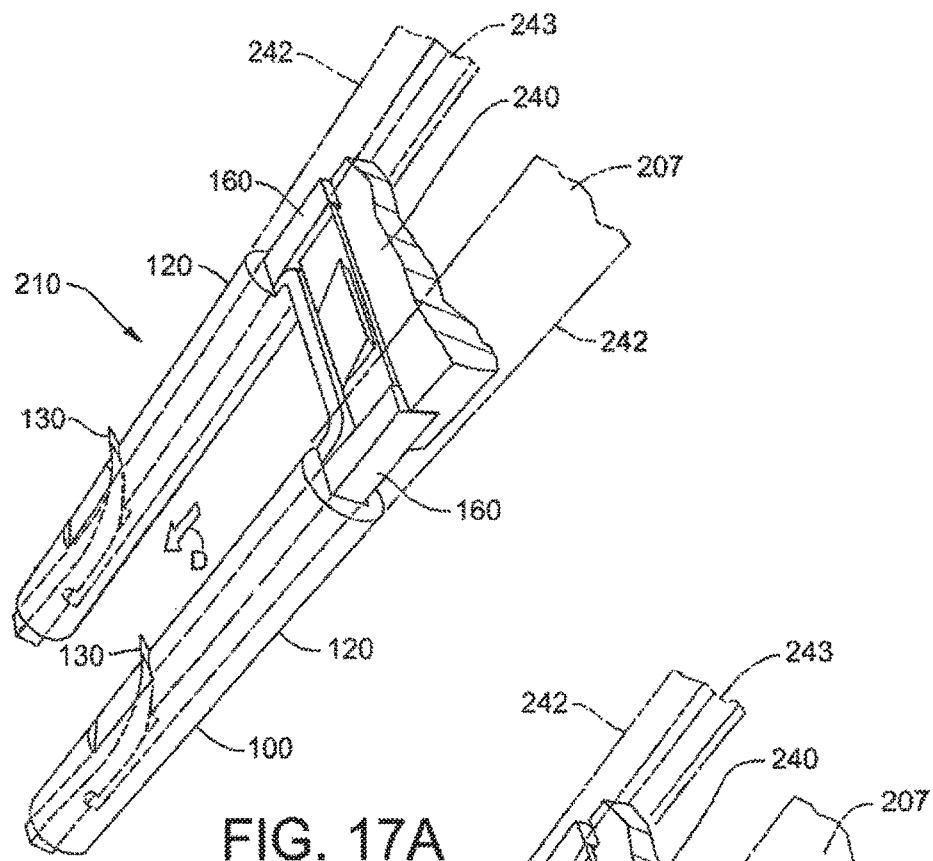
FIGS. 17A-17B are partial perspective views of the distal portion of a staple delivery device illustrating deployment of tissue retention members while holding the staple in a desired position.
Figure 17B:
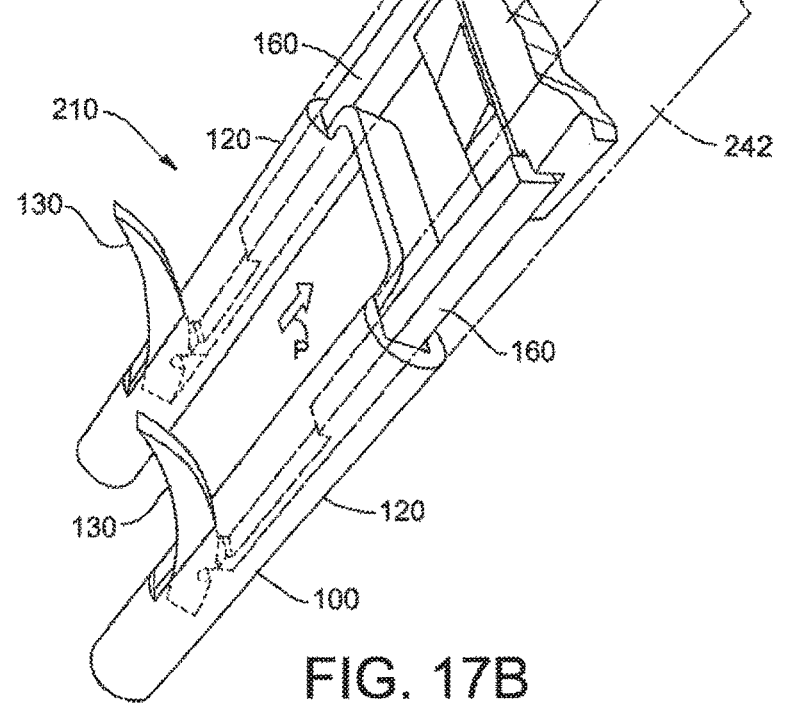

Now referring to FIGS. 17A-17B, a perspective view of a distal portion 207 of a staple delivery assembly 210 is illustrated. The staple delivery assembly 210 would be slidably disposed within a barrel 205 of a staple delivery device 200 as previously depicted in FIG. 15A. A staple 100 of the present disclosure is shown mounted on the distal portion 207 and the barrel is not shown to better view operation of the staple delivery device 200 in deploying a staple within bone. As previously discussed, staples of the present disclosure can be flexible and further are particularly useful in affixing an implant to bone. As such, the staples cannot be pounded in bone like a conventional staple. Therefore a method and apparatus for forming pilot holes has been disclosed that can be used with a staple delivery device that places the staple in the pilot holes so that claws can be extended to interact with the bone and provide holding strength to the staple.

FIGS. 17A and 17B depict a mechanism included on at least some staple delivery devices 200 that holds the staple in proper position while the claws are deployed into the bone. In FIG. 17A staple 100 having claws 130 disposed within the trunks 120 in a retracted position is illustrated. Further, pull members 160 are illustrated in engagement with a notch in claws 130. The pull members 160 are releasably attached to a deployment rod 240 which is only partially depicted. In a staple delivery device 200, such as that depicted in FIG. 15A, the deployment rod would extend proximally into the handle assembly and be mechanically coupled to the trigger such that squeezing the trigger causes the deployment rod 240 to retract proximally pulling on the pull members 160. Also depicted in FIG. 17A are staple setting rods 242. These are shown in phantom so as not to obscure the other features of the distal portion of the staple delivery device. The staple setting rods engage a proximal surface 243 of the trunks 120 and extend through the barrel to the handle. Further, in the embodiment depicted, the deployment rod travels in grooves 243 formed into the staple setting rods. The combination of the pull members 160, deployment rod 240 and staple setting rods 242 provide longitudinal support and strength for the staple to be inserted into the pilot holes in bone. The staple setting rods urge the staple into position within the pilot holes and continue to hold it there while the deployment rod 240 is retracted. This is shown in FIG. 17B where it can be seen that claws 130 have been deployed by retraction of the deployment rod 240 while the staple setting rods remain engaged with the proximal surfaces.

Figure 18A:
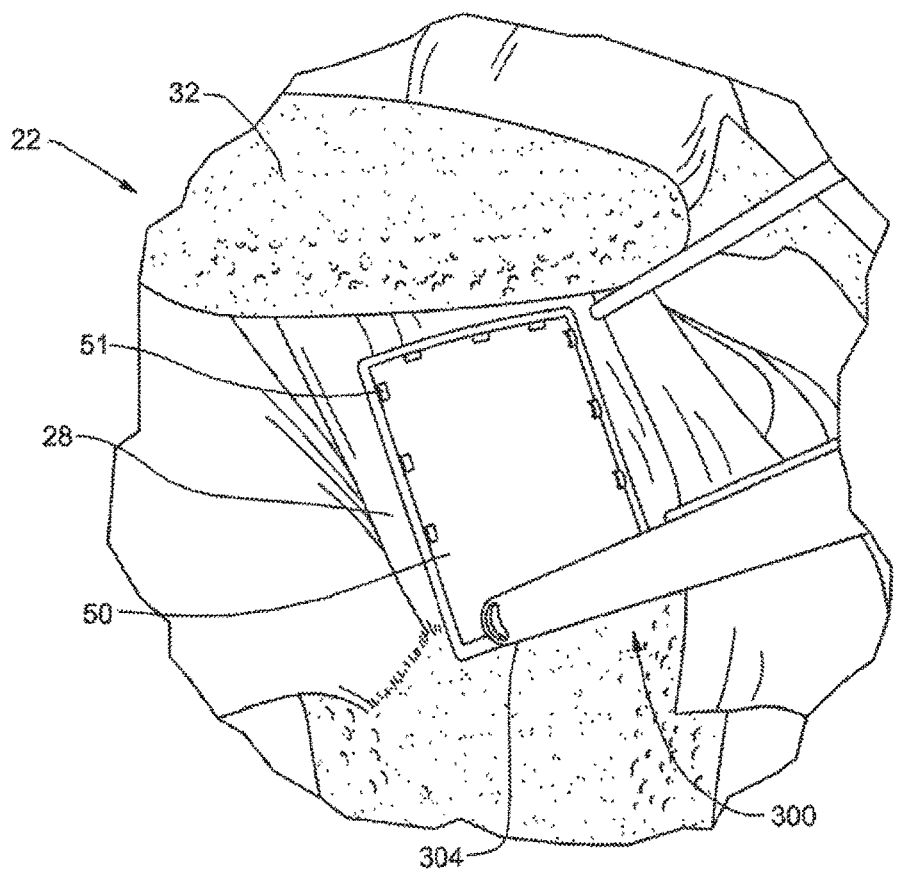
FIG. 18A is simplified perspective view of a shoulder having an implant affixed to the tendon and depicting the first step in a method of delivering fasteners to affix the implant to bone of the humeral head in accordance with one method of the disclosure.

A process of forming pilot holes and delivery of staples of the present disclosure to bone is described with respect to FIGS. 18A-18F which depict the various steps in affixing an implant 50 to bone with staples or fasteners of the present disclosure. FIG. 18A schematically depicts a shoulder 22 of a patient 20 having an implant 50 positioned over a supraspinitus tendon 28. The implant is partially affixed to the tendon 28 with fasteners 51 and extends laterally to and over the insertion point of the tendon to the humeral head 24. As depicted, the implant 50 is not yet affixed to the humeral head 24. A distal portion of a pilot hole forming trocar assembly 300, in particular the position retention sleeve 304, is disposed over a desired location near the lateral edge of the implant 50 where it overlies the humeral head 24. It is noted the FIG. 18A is a depiction with all overlying tissue removed from the shoulder 22 to clearly show the location of the entire implant 50 on the supraspinitus tendon 28. This view is typically not possible during actual arthroscopic procedures in which the fasteners and instruments of the present disclosure can be used, however the depiction provides a clear understanding of the placement of an implant and the use of fasteners disclosed herein. In actual use the surgeon will typically have a side view from a viewing scope (not shown) of a small space created by inflating the area with fluid and clearing necessary obstructions from the implant area.

Figure 18B:
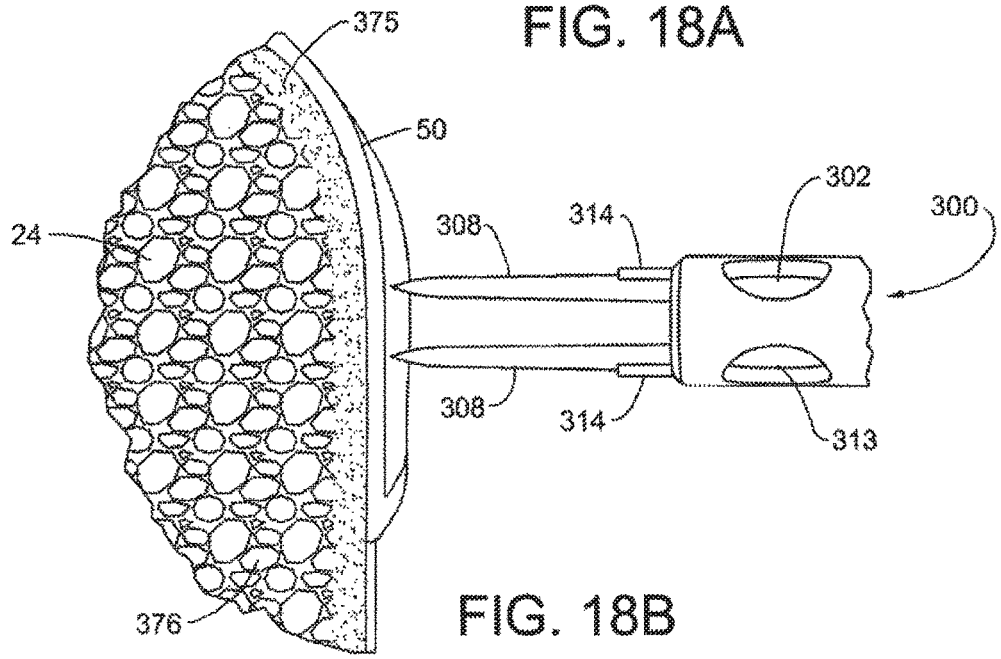
FIG. 18B is a simplified plan view of the distal portion of the trocar assembly as positioned to create pilot holes for affixing the implant to bone in a further step of a method of the disclosure.

FIG. 18B is a schematic illustration of a cross-sectional side view of the partially affixed implant of FIG. 18A showing the small portion of the implant 50 that is not yet affixed to the humeral head 24. As can be seen in the illustration, the humeral head 24 is shown in cross-section which illustrates the composite nature of bone structure. In general, bone includes hard outer portion or cortical layer 375 and a porous softer inner portion or cancellous bone 376. The pilot hole forming trocar assembly 300 is positioned with the spikes 308 over a selected position on the implant 50. As previously discussed, the trocar 302 is positioned within the lumen of the position retention sleeve 304 with spikes 308 extending distally. The spikes 308 can be used to manipulate and position the implant as needed. Once in position, the spikes 308 can be driven into the bone.

Figure 18C:
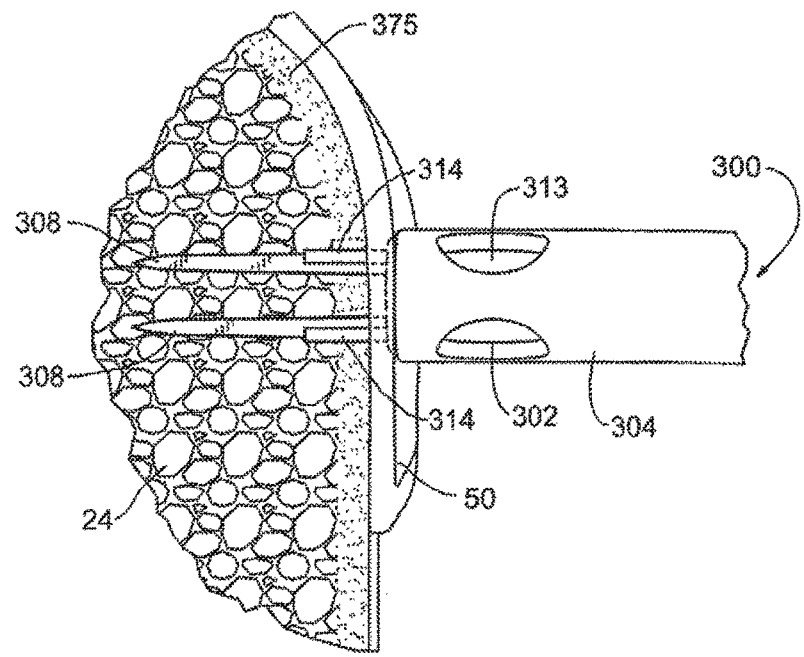
FIG. 18C depicts the trocar assembly of FIG. 18B as inserted into the bone to form pilot holes in accordance with a method of the disclosure.
Figure 18D:
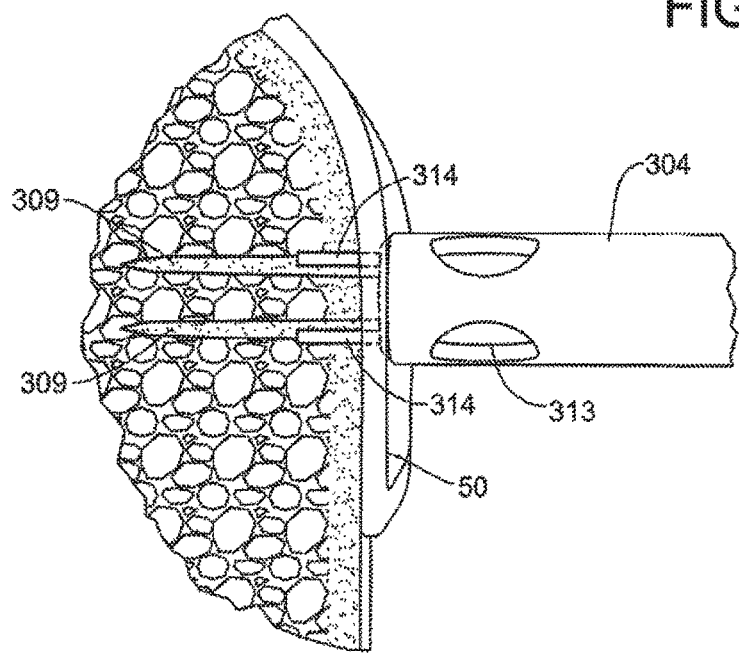
FIG. 18D depicts the trocar assembly with the trocar portion removed and the remaining sheath assembly retaining its position in the pilot holes formed.
Figure 18E:
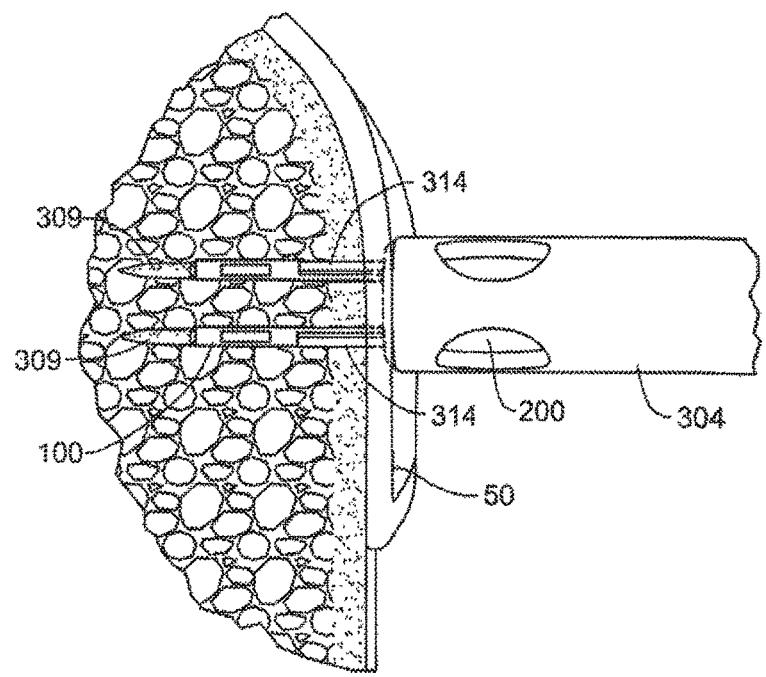
FIG. 18E depicts insertion of a fastener or staple into the formed pilots holes through the sheath assembly in accordance with a method of the disclosure; and, FIG. 18F illustrates a fastener or staple as inserted in accordance with a method of the disclosure.
Figure 18F:
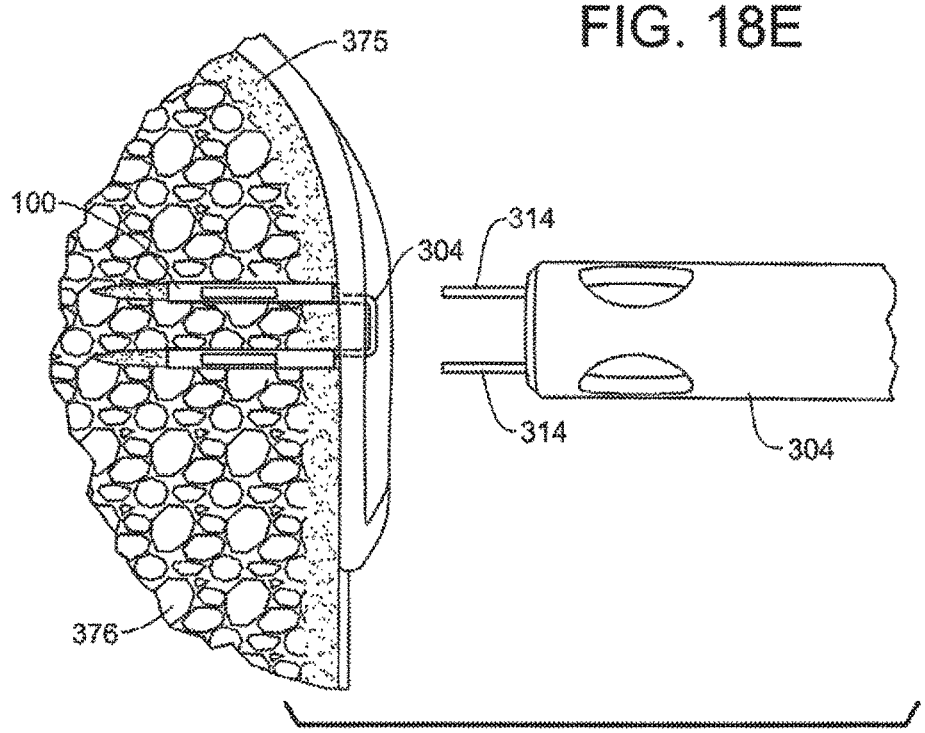

Referring to FIG. 18C, the illustration of FIG. 18B is re-illustrated with the pilot hole forming trocar 300 spikes pounded or otherwise driven into the humeral head 24, penetrating the cortical layer 375 into the cancellous portion 376. As illustrated, position retention members 314 also penetrate the bone with the spikes 308. In FIG. 18D, it is illustrated that the trocar 302 and its distal spikes 308 are now removed leaving formed pilot holes 309 with the position retention sleeve 304 remaining in position with position retention member 314 extending into pilot holes 309. The position retention member 304 lumen provides a guide to the pilot holes 309 for a staple delivery device 200. In FIG. 18E, a staple 100 is shown extending into the pilot holes 309 as mounted on the distal end of a staple delivery device 200 that has been inserted into the lumen of position retention member 304. In this position the staple can be delivered and retained in the bone as previously described in the various embodiments disclosed herein. FIG. 18F depicts a staple 100 as delivered into bone with bridge 304 holding the implant in position on the bone and arms of the staple retaining position in the bone, such as within the cancellous portion 376.

While exemplary embodiments of the present invention have been shown and described, modifications may be made, and it is therefore intended in the appended claims and subsequently filed claims to cover all such changes and modifications which fall within the true spirit and scope of the invention.

What is claimed is:
1. A method for affixing an implant to tissue comprising:
   positioning the implant proximate the tissue;
   penetrating both the implant and the tissue with a multicomponent fastener, the multicomponent fastener comprising:
   a first elongated trunk portion;
   a second elongated trunk portion;
   a bridge portion connecting the first elongated trunk portion and the second elongated trunk portion in a monolithic structure, wherein the first elongated trunk portion and the second elongated trunk portion are spaced apart and extend in a distal direction from the bridge portion, wherein the first elongated trunk portion and the second elongated trunk portion each define an axial lumen surrounded by a wall, each wall including a lateral aperture completely through the wall;

a first elongated retention member disposed within the axial lumen of the first elongated trunk portion, the first elongated retention member having a proximal tip and a distal tail;

a second elongated retention member disposed within the axial lumen of the second elongated trunk portion, the second elongated retention member having a proximal tip and a distal tail;

moving each of the first elongated retention member and the second elongated retention member from a retracted position in which the proximal tip is positioned within the lateral aperture to an extended position in which a portion of the distal tail of each retention member extends through the lateral aperture and away from the multicomponent fastener thereby engaging the tissue and affixing the implant to the tissue.

2. The method of claim 1, wherein the first elongated retention member and the second elongated retention member each are curved and tapered.

3. The method of claim 2, wherein the first elongated retention member and the second elongated retention member each include a notch.

4. The method of claim 3, further comprising a first deployment member configured and adapted to move the first elongated retention member from the retracted position to the extended position; and a second deployment member configured and adapted to move the second elongated retention member from the retracted position to the extended position.

5. The method of claim 4, wherein the first deployment member is configured and adapted to engage the notch of the first elongated retention member and the second deployment member is configured and adapted to engage the notch of the second elongated retention member.

6. The method of claim 5, further comprising retracting the first deployment member to move the first elongated retention member from the retracted position to the extended position, whereupon the first deployment member disengages from the first elongated retention member and retracting the second deployment member to move the second elongated retention member from the retracted position to the extended position, whereupon the second deployment member disengages from the first elongated retention member.

7. The method of claim 6, wherein moving the first elongated retention member from the retracted position to the extended position in which the distal tail of the first elongated retention member extends in a direction transverse to the axial lumen of the first elongated trunk portion.

8. The method of claim 6, wherein moving the second elongated retention member from the retracted position to the extended position in which the distal tail of the second elongated retention member extends in a direction transverse to the axial lumen of the second elongated trunk portion.

9. The method of claim 6, wherein the first elongated trunk portion, the second elongated trunk portion, and the bridge portion define a plane, wherein the first elongated retention member extends laterally from the plane in the extended position.

10. The method of claim 9, wherein the second elongated retention member extends laterally from the plane in the extended position.

11. The method of claim 2, wherein the first elongated retention member and the second elongated retention member each further include an enlarged distal head.

12. The method of claim 11, wherein the enlarged distal head of the first elongated retention member and the enlarged distal head of the second elongated retention member each further include a hole.

13. The method of claim 12, further comprising a first deployment member configured and adapted to move the first elongated retention member from the retracted position to the extended position; and a second deployment member configured and adapted to move the second elongated retention member from the retracted position to the extended position.

14. The method of claim 13, wherein the first deployment member is configured and adapted to engage the hole of the enlarged distal head of the first elongated retention member and the second deployment member is configured and adapted to engage the hole of the enlarged distal head of the second elongated retention member.

15. The method of claim 14, further comprising retracting the first deployment member to move the first elongated retention member from the retracted position to the extended position, whereupon the first deployment member disengages from the first elongated retention member and retracting the second deployment member to move the second elongated retention member from the retracted position to the extended position, whereupon the second deployment member disengages from the first elongated retention member.

16. The method of claim 11, wherein the first elongated trunk portion and the second elongated trunk portion each further comprise a second lateral aperture on a portion of the wall of the respective first elongated trunk portion and the second elongated trunk portion opposite the respective lateral apertures.

17. The method of claim 16, wherein moving the first elongated retention member from the retracted position to the extended position in which the enlarged distal head of the first elongated retention member extends in a direction transverse to the axial lumen of the first elongated trunk portion.

18. The method of claim 16, wherein moving the second elongated retention member from the retracted position to the extended position in which the enlarged distal head of the second elongated retention member extends in a direction transverse to the axial lumen of the second elongated trunk portion.

19. The method of claim 16, wherein moving the first elongated retention member from the retracted position to the extended position causes the enlarged distal head of the first elongated retention member to partially engage the second lateral aperture of the first elongated trunk portion and wherein moving the second elongated retention member from the retracted position to the extended position causes the enlarged distal head of the second elongated retention member to partially engage the second lateral aperture of the second elongated trunk portion.

20. The method of claim 16, wherein the first elongated trunk portion, the second elongated trunk portion, and the bridge portion define a plane, wherein the first elongated retention member and the second elongated retention member extends laterally from the plane in the extended position.

* * * * *